United States Patent
Tobinick

(10) Patent No.: US 7,629,311 B2
(45) Date of Patent: *Dec. 8, 2009

(54) METHODS TO FACILITATE TRANSMISSION OF LARGE MOLECULES ACROSS THE BLOOD-BRAIN, BLOOD-EYE, AND BLOOD-NERVE BARRIERS

(75) Inventor: Edward Lewis Tobinick, 100 UCLA Medical Plz., Suite 205, Los Angeles, CA (US) 90095

(73) Assignee: Edward Lewis Tobinick, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/601,799

(22) Filed: Nov. 17, 2006

(65) Prior Publication Data

US 2007/0196375 A1    Aug. 23, 2007

Related U.S. Application Data

(63) Continuation-in-part of application No. 11/016,047, filed on Dec. 18, 2004, now Pat. No. 7,214,658, which is a continuation-in-part of application No. 10/269,745, filed on Oct. 9, 2002, now Pat. No. 6,982,089, which is a continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/563,651, filed on May 2, 2000, now Pat. No. 6,471,961, which is a continuation-in-part of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(60) Provisional application No. 60/738,331, filed on Nov. 18, 2005, provisional application No. 60/760,236, filed on Jan. 18, 2006, provisional application No. 60/662,744, filed on Mar. 16, 2005, provisional application No. 60/585,735, filed on Jul. 6, 2004.

(51) Int. Cl.
*A61K 38/00* (2006.01)
*A61K 45/00* (2006.01)
*A61K 39/00* (2006.01)
*A61K 39/395* (2006.01)

(52) U.S. Cl. .................. 514/2; 424/145.1; 424/134.1; 424/85.1; 424/1.41; 424/1.49; 435/335

(58) Field of Classification Search .................. None
See application file for complete search history.

(56) References Cited

OTHER PUBLICATIONS

Tobinick and Gross, J Neuroinflam 5: 1-10, 2008.*
W Sue T Griffin J Neuroinflamm 5: 1-3, 2008.*

* cited by examiner

*Primary Examiner*—Jeffrey Stucker
*Assistant Examiner*—Aditi Dutt
(74) *Attorney, Agent, or Firm*—Ezra Sutton

(57) ABSTRACT

A method for delivering a biologic to a human with Alzheimer's-related dementia, comprising administering the biologic parenterally into the perispinal space of the human without direct intrathecal injection, and thereafter positioning the human's head below the horizontal. The method further includes delivering a TNF antagonist to the brain of a human for treating mild cognitive impairment, Alzheimer's related dementia, or vascular dementia, comprising administering the TNF antagonist golimumab parenterally into the perispinal space of the human without direct intrathecal injection, and thereafter positioning the human in a Trendelenburg position, for delivery of the golimumab to the brain via the human's vertebral venous system.

7 Claims, No Drawings

METHODS TO FACILITATE TRANSMISSION OF LARGE MOLECULES ACROSS THE BLOOD-BRAIN, BLOOD-EYE, AND BLOOD-NERVE BARRIERS

1. RELATED APPLICATIONS

This is a continuation-in-part of U.S. patent application Ser. No. 11/016,047, filed Dec. 18, 2004 now U.S. Pat. No. 7,214,658, entitled "Methods of delivering a TNF antagonist to the brain of a human by perispinal administration without direct intrathecal injection", which is a continuation-in-part of U.S. Patent Application 20030049256, also known as U.S. patent application Ser. No. 10/269,745, entitled "Cytokine antagonists for neurological and neuropsychiatric disorders", filed Oct. 9, 2002, now U.S. Pat No. 6,982,089, which is a continuation-in-part of Ser. No. 10/236,097, filed on Sep. 6, 2002, now abandoned, which is a continuation-in-part of application Ser. No. 09/841,844, filed on Apr. 25, 2001, now U.S. Pat. No. 6,357,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000 now U.S. Pat. No. 6,471,961, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned. This application is also related to provisional U.S. patent application 60/662,744 entitled "Methods of Use of the Vertebral Venous System to Deliver Biologics to the CNS" filed Mar. 16, 2005. In addition to the above, this application claims priority from U.S. provisional application 60/585,735, filed Jul. 6, 2004; U.S. provisional application 60/738,331, entitled "Methods to facilitate transmission of golimumab and other therapeutic molecules across the blood-brain barrier", filed Nov. 18, 2005; and U.S. provisional application entitled "Methods to facilitate transmission of golimumab and other therapeutic molecules across the blood-brain, blood-eye, and blood-nerve barriers", 60/760,236, filed Jan. 18, 2006, all of which are hereby incorporated by reference in their entirety herein. The use of perispinal administration of cytokine antagonists to treat neurological disorders is discussed in US patent application 20030049256 of this inventor. The use of perispinal administration without direct intrathecal injection and the vertebral venous system to deliver large molecules to the brain, the eye, and the auditory apparatus are discussed in provisional patent applications 60/585,735 filed Jul. 6, 2004; 60/659,414 filed Mar. 9, 2005; 60/662,744 filed Mar. 17, 2005; and 60/669,022, filed Apr. 7, 2005. All of the above patents and patent applications included in this paragraph are incorporated by reference in their entirety herein.

2. FIELD OF THE INVENTION

This application concerns novel methods which enable golimumab, an anti-TNF biologic and other molecules, to cross the blood-brain barrier, the blood-eye barrier, and/or the blood-nerve barrier and therefore be of therapeutic use in humans and other mammals. These methods involve perispinal administration of each of these molecules without direct intrathecal injection. Perispinal administration is defined as administration of the molecule into the anatomic area within 10 cm of the spine. Perispinal administration results in absorption of golimumab into the vertebral venous system. The vertebral venous system is capable of transporting molecules to the head, including into the brain, the eye, the retina, the auditory apparatus, the cranial nerves or the head, via retrograde venous flow, thereby bypassing the blood-brain barrier and delivering the molecules to the brain, the eye, the retina, the auditory apparatus, the cranial nerves or the head.

This method may be utilized for a wide variety of large molecules, including, but not limited to, recombinant DNA therapeutics, other biologics, monoclonal antibodies, fusion proteins, monoclonal antibody fragments, hormones, cytokines, anti-cytokines, interleukins, anti-interleukins, interferons, colony-stimulating factors, cancer chemotherapeutic agents, growth factors, anti-virals and antibiotics.

In addition the methods of the present invention may be used to deliver molecules with a MW less than 2,000 daltons to the brain and other structures of the head more efficiently than if delivered systemically, and these methods utilizing these molecules are also to be considered a part of this invention.

In addition to human use, these methods may be used to treat other mammals, including horses, dogs, and cats.

This method may be used for delivery for humans or other mammals with neurodegenerative diseases, including Alzheimer's Disease and other forms of dementia, including both Alzheimer's-related dementia and non-Alzheimer dementias; Parkinson's Disease, amyotrophic lateral sclerosis; for eye disorders or diseases including, but not limited to, macular degeneration, diabetic retinopathy, sympathetic opthalmia and retinitis pigmentosa; disorders of hearing, including, but not limited to sensorineural hearing loss or presbycusis; central nervous system (CNS) tumors, including tumors of the brain; for other diseases or disorders of the brain, including, but not limited to vascular disorders such as stroke, transient ischemic attack, vascular dementia, and cerebrovascular disease; infectious diseases of the CNS, including viral and bacterial infections; for sciatica, cervical radiculopathy, and other forms of disc-related pain; for low back pain; other diseases or disorders involving the spine, the spinal cord, the spinal nerve roots, the brain, eyes, auditory apparatus, or other structures of the head.

The use of cytokine antagonists to treat neurological disorders is the subject of several previous patents of this inventor, including U.S. Pat. Nos. 6,015,557, 6,177,077, 6,419,934 6,419,944, 6,423,321, 6,428,787, 6,537,549, 6,623,736 and US patent applications 20030049256 and U.S. patent application Ser. No. 11/016,047, filed Dec. 18, 2004, entitled "Methods of use of etanercept to improve human cognitive function", and provisional U.S. patent application 60/585, 735, filed Jul. 6, 2004. These issued patents, patent applications, and provisional patent applications are incorporated in their entirety herein. This invention includes further applications of these ideas.

The adverse biologic effects of excess TNF can be reduced by the use of biologic inhibitors of TNF. These inhibitors can be divided into two broad categories: monoclonal antibodies and their derivatives; and TNF binding biologics which are not antibody based. In the first category belong golimumab, also known as CNTO-148(Centocor, Schering-Plough), infliximab (Remicade®, Centocor), adalimumab (Humira®, Abbott), and CDP 870 (Celltech). The second category includes etanercept, soluble TNF receptor type 1, pegylated soluble TNF receptor type 1 (Amgen) and onercept (Serono). Etanercept has a serum half life of approximately 4.8 days when administered to patients with rheumatoid arthritis on a chronic basis; onercept has a serum half-life which is considerably shorter, and it is usually administered at least three times weekly when used to treat systemic illnesses.

Golimumab has many biologic effects. Golimumab, for example, in addition to being a potent anti-inflammatory also has important anti-apoptotic effects which may be of particular importance in treating neurological disorders, such as certain forms of dementia, where apoptosis plays a pathogenetic role.

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Monoclonal antibodies, fusion proteins, and all of the specific molecules discussed above under the categories of TNF antagonists and interleukin antagonists are considered biologics, in contrast to drugs that are chemically synthesized. For the purpose of this patent a biologic is defined as a molecule produced through recombinant DNA technology which is derived from the DNA of a living source. The living sources may include humans, other animals, or microorganisms. The biologics mentioned above are manufactured using biotechnology, which usually involves the use of recombinant DNA technology. Cytokine antagonists are one type of biologic. Biologics are regulated through a specific division of the FDA.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel®).

TNF, a naturally occurring cytokine present in humans and other mammals, plays a key role in the inflammatory response, in the immune response and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Golimumab is currently in clinical development by Centocor/Schering-Plough for treatment of rheumatoid arthritis, with potential applications for uveitis, asthma, and Crohn's Disease. It may be described as a immunoglobulin G1, anti-(human tumor necrosis factor α) (human monoclonal CNTO 148 γ1-chain), disulfide with human monoclonal CNTO 148 κ-chain), dimer, and has CAS Registry number 476181-74-5. It is a fully human anti-TNF monoclonal antibody.

Etanercept (Enbrel®, Amgen/Immnunex), golimumab, infliximab (Remicade®, Centocor), adalimumab (Humira®, Abbott), CDP 870, and onercept are potent and selective inhibitors of TNF. CDP 870, golimumab and onercept are in clinical development. Etanercept, adalimumab, and infliximab are FDA approved for chronic systemic use to treat rheumatoid arthritis and certain other chronic inflammatory disorders. Golimumab has a molecular weight of approximately 147,000 daltons.

Bevacizumab (Avastin™, Genentech) is a recombinant humanized monoclonal IgG1 antibody that binds to and inhibits the biologic activity of human vascular endothelial growth factor (VEGF) and which may be useful for the treatment of various malignancies. Bevacizumab has a molecular weight of 149,000 daltons and is therefore too large to readily cross the blood-brain barrier if administered systemically.

Anti-amyloid antibodies of the present invention include immune globulin derived from human plasma, including Gammagard™ and Kiovig™ brands of IVIG produced by Baxter and other brands of IVIG; antibodies against beta-amyloid; and, specifically, Bapineuzumab, a humanized monoclonal antibody to A-beta currently being jointly developed by Elan and Wyeth.

Etanercept, one of the molecules of this invention, can also be designated as TNFR:Fc because it is a dimeric fusion protein consisting of two soluble TNF receptors fused to a Fc portion of an immunoglobulin molecule. This fusion protein functions in a manner quite distinct from a simple soluble TNF receptor. Soluble TNF receptors are normally present in the human body. But the use of these soluble TNF receptors as therapeutic agents for the treatment of the conditions of consideration in this patent is made impractical by their extremely short half-life and therefore their limited biologic activity. The present invention utilizing etanercept is therefore distinguished from an invention specifying the use of a soluble TNF receptor. It is incorrect and imprecise to describe etanercept as a soluble TNF receptor because this is an incorrect description of its complex structure and omits characteristics of etanercept which are absolutely essential to its function. This is further underscored by the developmental history of etanercept. In its first iteration the precursor molecule to etanercept was produced with a single TNF receptor fused to an immunoglobulin fragment. The biologic activity of this molecule was poor. Therefore not only is etanercept distinguished from a soluble TNF receptor, it is also distinguished from a TNF-binding fusion protein which contains the recombinant DNA sequence of only a single soluble TNF receptor. The unique structure of etanercept, containing a dimer (two) soluble TNF receptors fused to an Fc portion of an immunoglobulin molecule, is necessary for the proper performance of the present invention. Since etanercept has the molecular structure of a fusion protein it is thus quite distinct from both onercept, soluble TNF receptor type 1 and pegylated soluble TNF receptor type 1.

The vertebral venous system can also be used to deliver other types of therapeutic agents to the cerebral cortex, eye, retina, cerebellum, brainstem, eighth cranial nerve, cochlea, inner ear, and cerebrospinal fluid. These therapeutic agents include pharmacologic agents, other cytokine antagonists, and growth factors which affect neuronal function, or the immune response impacting neuronal function, including, but not limited to: interleukins including IL-1, IL-2, IL-4, IL-6, IL-10, and IL-13; interleukin 1 antagonists, such as IL-1 RA (Kineret®, Amgen) and IL-1 Trap; fusion proteins, such as IL-10 fusion protein and etanercept (Enbrel®, Immunex); human growth hormone and related biologics (recombinant human growth hormone, Humatrope®) (somatropin) Eli Lilly & Co., Nutropin®/Nutropin AQ® (somatropin), Geref® (sermorelin) Serono, and Protropin® (somatrem) Genentech)); BDNF; erythropoietin (Epogen® (epoetin alpha) Amgen, Procrit® (epoetin alpha) Johnson & Johnson); G-CSF (Neupogen® (filgrastim), Amgen); GM-CSF; Intron® A (interferon alfa-2b) Schering-Plough; Avonex® (interferon beta-1a) Biogen; bevacizumab (Avastin™, Genentech); pegaptanib, ranibizumab, and other biologic VEGF antagonists; alefacept (LFA-3/IgG1 human fusion protein, Amevive® Biogen); Epidermal growth factor; anti-EGF (ABX-EGF, Abgenix); transforming growth factor-beta 1 (TGF-beta 1); NGF, or other compounds with CNS, vascular or immune therapeutic activity. Perispinal delivery is particularly advantageous when biologics, such as etanercept, which profoundly affect neuronal function, are administered because of their efficacy at extremely low concentration (high biologic potency).

This method may be used for delivery for humans or other mammals with neurodegenerative diseases, including Alzheimer's Disease, other forms of Alzheimer-related dementia, non-Alzheimer dementia, Parkinson's Disease, and amyotrophic lateral sclerosis; for eye disorders or diseases including, but not limited to, macular degeneration, diabetic retinopathy, sympathetic opthalmia and retinitis pigmentosa; disorders of hearing, including, but not limited to sensorineural hearing loss or presbycusis; central nervous system (CNS) tumors, including tumors of the brain; for other diseases or disorders of the brain, including, but not limited to vascular disorders such as stroke, transient ischemic attack, vascular dementia, and cerebrovascular disease; infectious diseases of the CNS, including viral and bacterial infections; for sciatica, cervical radiculopathy, and other forms of disc-related pain; for low back pain; other diseases or disorders involving the spine, the spinal cord, the spinal nerve roots, the brain, eyes, auditory apparatus, or other structures of the head.

3. BACKGROUND OF THE INVENTION

The following description of the background of the invention is provided as an aid to understanding the invention and is not admitted to describe or constitute prior art to the invention.

This application concerns novel methods which enable golimumab, an anti-TNF biologic and other molecules, to cross the blood-brain barrier, the blood-eye barrier, and/or the blood-nerve barrier and therefore be of therapeutic use in humans and other mammals. Included among these methods are those which involve perispinal administration of golimumab without direct intrathecal injection. In addition, additional methods involve the perispinal administration of other molecules, as detailed herein. Perispinal administration is defined as administration of the molecule into the anatomic area within 10 cm of the spine. Perispinal administration results in absorption of golimumab or other molecules given by perispinal administration, into the vertebral venous system. The vertebral venous system is capable of transporting therapeutic molecules to the head, including into the brain, the eye, the retina, the auditory apparatus, the cranial nerves or the head, via retrograde venous flow, thereby bypassing the blood-brain barrier and delivering the molecules to the brain, the eye, the retina, the auditory apparatus, the cranial nerves or the head.

This method may be utilized for a wide variety of large molecules, including, but not limited to, recombinant DNA therapeutics, other biologics, monoclonal antibodies, fusion proteins, monoclonal antibody fragments, hormones, cytokines, anti-cytokines, interleukins, anti-interleukins, interferons, colony-stimulating factors, cancer chemotherapeutic agents, growth factors, anti-virals and antibiotics.

In addition the methods of the present invention may be used to deliver molecules with a MW less than 2,000 daltons to the brain and other structures of the head more efficiently than if delivered systemically, and these methods utilizing these smaller molecules are also to be considered a part of this invention.

In addition to human use, these methods may be used to treat other mammals, including horses, dogs, and cats.

This method may be used for delivery for humans or other mammals with neurodegenerative diseases, including Alzheimer's Disease, Parkinson's Disease, amyotrophic lateral sclerosis; for eye disorders or diseases including, but not limited to, macular degeneration, diabetic retinopathy, sympathetic opthalmia and retinitis pigmentosa; disorders of hearing, including, but not limited to sensorineural hearing loss or presbycusis; central nervous system (CNS) tumors, including tumors of the brain; for other diseases or disorders of the brain, including, but not limited to vascular disorders such as stroke, transient ischemic attack, vascular dementia, and cerebrovascular disease; infectious diseases of the CNS, including viral and bacterial infections; for sciatica, cervical radiculopathy, and other forms of disc-related pain; for low back pain; other diseases or disorders involving the spine, the spinal cord, the spinal nerve roots, the brain, eyes, auditory apparatus, or other structures of the head.

The use of cytokine antagonists to treat neurological disorders is the subject of several previous patents of this inventor, including U.S. Pat. Nos. 6,015,557, 6,177,077, 6,419,934 6,419,944, 6,423,321, 6,428,787, 6,537,549, 6,623,736 and US patent applications 20030049256 and U.S. patent application Ser. No. 11/016,047, filed Dec. 18, 2004, entitled "Methods of use of etanercept to improve human cognitive function", and provisional U.S. patent application 60/585, 735, filed Jul. 6, 2004. These issued patents, patent applications, and provisional patent applications are incorporated in their entirety herein. This invention includes further applications of these ideas.

The adverse biologic effects of excess TNF can be reduced by the use of biologic inhibitors of TNF. These inhibitors can be divided into two broad categories: monoclonal antibodies and their derivatives; and TNF binding biologics which are not antibody based. In the first category belong golimumab, also known as CNTO-148 (Centocor, Schering-Plough), infliximab (Remicade®, Centocor), adalimumab (Humira®, Abbott), and CDP 870 (Celltech). The second category includes etanercept, soluble TNF receptor type 1, pegylated soluble TNF receptor type 1 (Amgen) and onercept (Serono). Etanercept has a serum half life of approximately 4.8 days when administered to patients with rheumatoid arthritis on a chronic basis; onercept has a serum half-life which is considerably shorter, and it is usually administered at least three times weekly when used to treat systemic illnesses.

Golimumab has many biologic effects. Golimumab, for example, in addition to being a potent anti-inflammatory also has important anti-apoptotic effects which may be of particular importance in treating neurological disorders, such as certain forms of dementia, where apoptosis plays a pathogenetic role.

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Monoclonal antibodies, fusion proteins, and all of the specific molecules discussed above under the categories of TNF antagonists and interleukin antagonists are considered biologics, in contrast to drugs that are chemically synthesized. For the purpose of this patent a biologic is defined as a molecule produced through recombinant DNA technology which is derived from the DNA of a living source. The living sources may include humans, other animals, or microorganisms. The biologics mentioned above are manufactured using biotechnology, which usually involves the use of recombinant DNA technology. Cytokine antagonists are one type of biologic. Biologics are regulated through a specific division of the FDA.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel®).

TNF, a naturally occurring cytokine present in humans and other mammals, plays a key role in the inflammatory response, in the immune response and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Golimumab is currently in clinical development by Centocor/Schering-Plough for treatment of rheumatoid arthritis, with potential applications for uveitis, asthma, and Crohn's Disease. It may be described as a immunoglobulin G1, anti-(human tumor necrosis factor α) (human monoclonal CNTO 148 γ1-chain), disulfide with human monoclonal CNTO 148 κ-chain), dimer, and has CAS Registry number 476181-74-5. It is a fully human anti-TNF monoclonal antibody.

Etanercept (Enbrel®, Amgen/Immunex), golimumab, infliximab (Remicade®, Centocor), adalimumab (Humira®, Abbott), CDP 870, and onercept are potent and selective inhibitors of TNF. CDP 870, golimumab and onercept are in clinical development. Etanercept, adalimumab, and infliximab are FDA approved for chronic systemic use to treat rheumatoid arthritis and certain other chronic inflammatory disorders. Golimumab has a molecular weight of approximately 147,000 daltons.

Bevacizumab (Avastin™, Genentech) is a recombinant humanized monoclonal IgG1 antibody that binds to and inhibits the biologic activity of human vascular endothelial growth factor (VEGF) and which may be useful for the treatment of various malignancies. Bevacizumab has a molecular weight of 149,000 daltons and is therefore too large to readily cross the blood-brain barrier if administered systemically.

Etanercept can also be designated as TNFR:Fc because it is a dimeric fusion protein consisting of two soluble TNF receptors fused to a Fc portion of an immunoglobulin molecule. This fusion protein functions in a manner quite distinct from a simple soluble TNF receptor. Soluble TNF receptors are normally present in the human body. But the use of these soluble TNF receptors as therapeutic agents for the treatment of the conditions of consideration in this patent is made impractical by their extremely short half-life and therefore their limited biologic activity. The present invention utilizing etanercept is therefore distinguished from an invention specifying the use of a soluble TNF receptor. It is incorrect and imprecise to describe etanercept as a soluble TNF receptor because this is an incorrect description of its complex structure and omits characteristics of etanercept which are absolutely essential to its function. This is further underscored by the developmental history of etanercept. In its first iteration the precursor molecule to etanercept was produced with a single TNF receptor fused to an immunoglobulin fragment. The biologic activity of this molecule was poor. Therefore not only is etanercept distinguished from a soluble TNF receptor, it is also distinguished from a TNF-binding fusion protein which contains the recombinant DNA sequence of only a single soluble TNF receptor. The unique structure of etanercept, containing a dimer (two) soluble TNF receptors fused to an Fc portion of an immunoglobulin molecule, is necessary for the proper performance of the present invention. Since etanercept has the molecular structure of a fusion protein it is thus quite distinct from both onercept, soluble TNF receptor type 1 and pegylated soluble TNF receptor type 1.

The vertebral venous system can also be used to deliver other types of therapeutic agents to the cerebral cortex, eye, retina, cerebellum, brainstem, eighth cranial nerve, cochlea, inner ear, and cerebrospinal fluid. These therapeutic agents include pharmacologic agents, other cytokine antagonists, and growth factors which affect neuronal function, or the immune response impacting neuronal function, including, but not limited to: interleukins including IL-1, IL-2, IL-4, IL-6, IL-10, and IL-13; interleukin 1 antagonists, such as IL-1 RA (Kineret®, Amgen) and IL-1 Trap; fusion proteins, such as IL-10 fusion protein and etanercept (Enbrel®, Immunex); human growth hormone and related biologics (recombinant human growth hormone, Humatrope® (somatropin) Eli Lilly & Co., Nutropin®/Nutropin AQ® (somatropin), Geref® (sermorelin) Serono, and Protropin® (somatrem) Genentech)); BDNF; erythropoietin (Epogen® (epoetin alpha) Amgen, Procrit® (epoetin alpha) Johnson & Johnson); G-CSF (Neupogen® (filgrastim), Amgen); GM-CSF; Intron® A (interferon alfa-2b) Schering-Plough; Avonex® (interferon beta-1a) Biogen; bevacizumab (Avastin™, Genentech); pegaptanib, ranibizumab, and other biologic VEGF antagonists; alefacept (LFA-3/IgG1 human fusion protein, Amevive® Biogen); Epidermal growth factor; anti-EGF (ABX-EGF, Abgenix); transforming growth factor-beta 1 (TGF-beta 1); NGF, or other compounds with CNS, vascular or immune therapeutic activity. Perispinal delivery is particularly advantageous when biologics, such as etanercept, which profoundly affect neuronal function, are administered because of their efficacy at extremely low concentration (high biologic potency).

This method may be used for delivery for humans or other mammals with neurodegenerative diseases, including Alzheimer's Disease, Parkinson's Disease, amyotrophic lateral sclerosis; for eye disorders or diseases including, but not limited to, macular degeneration, diabetic retinopathy, sympathetic opthalmia and retinitis pigmentosa; disorders of hearing, including, but not limited to sensorineural hearing loss or presbycusis; central nervous system (CNS) tumors, including tumors of the brain; for other diseases or disorders of the brain, including, but not limited to vascular disorders such as stroke, transient ischemic attack, vascular dementia, and cerebrovascular disease; infectious diseases of the CNS, including viral and bacterial infections; for sciatica, cervical radiculopathy, and other forms of disc-related pain; for low back pain; other diseases or disorders involving the spine, the spinal cord, the spinal nerve roots, the brain, eyes, auditory apparatus, or other structures of the head.

Localized administration for the treatment of localized clinical disorders has many clinical advantages over the use of conventional systemic treatment. Locally administered medication after delivery diffuses through local capillary, venous, arterial, and lymphatic action to reach the therapeutic target. In addition local administration of a large molecule, such as goliumumab, defined as a molecule with a molecular weight greater than or equal to 2,000 daltons, in the vicinity of the spine (perispinal administration) without direct intrathecal injection has the key advantage of improved delivery of the molecule to the brain and across the blood-brain barrier (BBB), with delivery enhanced by transport via the vertebral venous system. Intrathecal injection delivers the molecule into the cerebrospinal fluid (CSF), but has disadvantages of possible infection, hemorrhage, and subsequent CSF leak.

The BBB is a physiologic barrier which separates the brain and cerebrospinal fluid from the blood. It consists of a layer of cells which comprise the cerebral capillary endothelium, the choroid plexus epithelium, and the arachnoid membranes, which are connected by tight junctions (zonulae occludens). These tight junctions may be as much as 100 times tighter than junctions of other capillary endothelium, and prevent molecules larger than about 600 daltons in molecular weight (MW) from traversing the BBB when the molecule is administered systemically i.e. by conventional subcutaneous, intramuscular, or intravenous injection at an anatomic site remote from the spine.

The vertebral venous system (VVS) is an interconnected plexus of veins which surrounds the spinal cord and extends the entire length of the spine. This venous system provides a vascular route from the pelvis to the cranium which richly involves the bone marrow of the spine and which is functionally distinct from the systemic venous system. First described by Willis in 1663, the functional significance of the vertebral venous system was largely unappreciated until the work of Batson, who in 1940 proposed that this venous plexus provided the route by which prostate cancer metastasizes to the vertebral column. Acceptance of Batson's proposal by the medical community has led to the designation of the vertebral venous system as Batson's Plexus. Although now widely appreciated as a possible route by which cancer cells may spread to the spine there have been no previous suggestions that Batson's plexus may be of therapeutic usefulness. The use of Batson's plexus as route of delivery of biologics for clinical use, and as a route for delivery of large molecules to the brain, the eye, the retina, the auditory apparatus, the cranial nerves or the head are inventions of the author. This patent is a continuation to the methods of use of Batson's plexus to deliver therapeutic molecules to the nervous system which has been previously proposed by the inventor, and incorporates the previous patents and patent applications discussing this. In addition this patent is related to provisional U.S. patent application 60/662,744 entitled "Methods of Use of the Vertebral Venous System to Deliver Biologics to the CNS" filed Mar. 16, 2005, and application Ser. No. 10/269, 745, entitled "Cytokine antagonists for neurological and neuropsychiatric disorders", filed Oct. 9, 2002, and each of these patent applications are hereby incorporated herein in their entirety.

Perispinal administration involves anatomically localized delivery performed so as to place the therapeutic molecule directly in the vicinity of the spine at the time of initial administration. For the purposes of this patent, "in the vicinity of" is defined as within 10 centimeters. Perispinal administration includes, but is not limited to, the following types of administration: parenteral; subcutaneous; intramuscular; or interspinous; and specifically includes the use of interspinous injection carried through the skin in the midline of the neck or back, directly overlying the spine.

For the purposes of this patent perispinal administration excludes intrathecal administration, which carries additional risks of infection and hemorrhage. Therefore in this patent "perispinal" is more exactly defined as "perispinal (extrathecal)", but for the purposes of brevity shall be designated throughout simply as "perispinal". Perispinal administration leads to enhanced delivery of large molecules to the brain and the head and the structures therein in a therapeutically effective amount. The conventional mode of delivery of these molecules for clinical applications, i.e. subcutaneous administration in the abdomen, thighs, or arms, does not effectuate delivery across the blood-brain barrier (see Robinson reference 60) which is as efficient as perispinal administration and is therefore distinguished from the perispinal methods of administration described in this invention.

Hearing loss occurs in humans in many forms. Hearing is essential to the normal conduct of one's daily activities and people with impaired hearing have many difficulties. Hearing loss can date from birth; it can be acquired later in life; or it can be the result of trauma, accident, disease, or a toxic effect of a medication. It can be genetic, either as a solitary disorder or as part of a complex syndrome. Hearing loss is one of the most common chronic neurological impairments, estimated to affect about 4 percent of those under 45 in the United States, and about 29 percent of those 65 years or older.

As defined herein, the auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids.

The pathogenetic mechanism of most forms of hearing loss has yet to be fully defined. Hearing loss can be due to conductive problems, which is not the subject of this patent; central hearing loss due to lesions of the central auditory pathway; or sensorineural hearing loss.

Humans react to sounds that are transduced into neurally conducted impulses through the action of neuroepithelial cells (hair cells) and spiral ganglion cells (neurons) in the inner ear. These impulses are transmitted along the cochlear division of the eighth cranial nerve into the brainstem and the central auditory pathways.

Presbycusis, or age-related hearing loss, is a type of sensorineural deafness which affects one-third of the population over the age of 75. The exact mechanism of presbycusis is unknown, and has long been thought to be multifactorial. Inflammation has not previously been thought to be a significant factor in the pathogenesis of presbycusis. Yet a previous study did suggest that genes encoded by the major histocompatibility complex (MHC) had a role in certain hearing disorders. (Bernstein, Acta Otolaryngol 1996 September; 116 (5):666-71). The MHC is known to be central to the immune response and inflammation.

As will be discussed below there is now clinical evidence that inflammation has a role in the pathogenesis of various types of sensorineural hearing loss, including presbycusis. This opens up a new avenue of treatment of these disorders utilizing large molecules delivered by perispinal administration without direct intrathecal injection, including biologic TNF inhibitors and other large molecules with a molecular weight equal to or greater than 2,000 daltons.

As discussed in the previous patents and patent applications of the inventor, including U.S. Pat. Nos. 6,082,089; 6,537,549, and the others as enumerated above, including those detailed in section 1 of this application, the methods of the present invention may be utilized to treat sciatica, cervical radiculopathy, fibromyalgia, severe low back pain and/or related pain conditions, including neuropathic pain.

4. DESCRIPTION OF THE PRIOR ART

Pharmacologic chemical substances, compounds and agents having various organic structures and metabolic functions which are used for the treatment of sensorineural hearing loss, and TNF related diseases have been disclosed in the prior art. One example is U.S. Pat. No. 5,837,681, entitled "Method For Treating Sensorineural Hearing Loss Using Glial Cell Line-Derived Neurotrophic Factor (GDNF) Protein Product". However, this prior art patent does not teach the use of a TNF antagonist delivered via the vertebral venous system, as in the present invention, and GDNF has biologic actions which are clearly distinct from those of the TNF binding biologics of the present invention.

U.S. Pat. No. 6,043,221 entitled "Method For Preventing And Treating Hearing Loss Using A Neuturin Protein Product" discusses the use of a neurotrophic factor. This prior art patent does not teach the use of a TNF antagonist delivered via the vertebral venous system to treat disorders of the brain, as in the present invention.

U.S. Pat. No. 5,385,901 entitled "Method Of Treating Abnormal Concentrations of TNF Alpha" discloses a method for the use of TNF antagonists. This prior art patent does not teach the use of a biologic delivered via the vertebral venous system as described in the present invention for the suppression and inhibition of the action of TNF in the human body to treat disorders of the brain, as in the present invention.

U.S. Pat. No. 5,434,170 entitled "Method For Treating Neurocognitive Disorders" discloses the use of thalidomide to treat dementia. This prior art patent does not teach the use of etanercept or another biologic delivered via the vertebral venous system as described in the present invention to treat disorders of the brain.

U.S. Patent No. 6,277,969 discloses the use of anti-TNF antibodies for treatment of various disorders. This prior art patent does not teach the use of etanercept or another biologic delivered via the vertebral venous system as described in the present invention to treat disorders of the brain.

U.S. Patent application 2004/0258671 by Watkins entitled "Methods for Treating Pain" discloses the use of IL-10 and IL-10 fusion protein and other biologics for treating pain. This patient application does not disclose the use of these substances to treat disorders of the brain.

U.S. Pat. No. 5,656,272 to LE et. al. discloses the use of TNF inhibitors for treatment of various disorders, including the use of anti-TNF monoclonal antibodies. This prior art patent does not teach the use of etanercept or another biologic delivered via the vertebral venous system as described in the present invention to treat disorders of the brain.

U.S. Pat. No. 5,650,396 discloses a method of treating multiple sclerosis(MS) by blocking and inhibiting the action of TNF in a patient. This prior art patent does not teach the use of etanercept or another biologic delivered via the vertebral venous system as described in the present invention to treat disorders of the brain.

U.S. Pat. No. 5,605,690 discloses the use of TNF inhibitors for treatment of various disorders. This prior art patent does not teach the use of etanercept or another biologic delivered via the vertebral venous system as described in the present invention to treat disorders of the brain.

U.S. patent application US 2003/0148955 to Pluenneke discloses the use of biologic TNF inhibitors, including etanercept, for the treatment of medical disorders. However, it does not give an enabling disclosure of the use of etanercept for the treatment of disorders of the brain utilizing the vertebral venous system as does the present invention and it does not predate the U.S. Pat. No. 6,015,557 of the present inventor of which this patent application is a continuation-in-part.

U.S. Pat. Nos. 7,115,557, 6,649,589 and 6,635,250 and related patent applications which have not been granted, to Olmarker and Rydevik, and previous publications by Olmarker (see References) discuss the use of TNF inhibitors for the treatment of nerve root injury and related disorders. These patents do not teach the use of etanercept or another biologic delivered via the vertebral venous system as described in the present invention to treat disorders of the brain, and are not enabling with respect to etanercept, golimumab, certolizumab pegol, and other molecules discussed herein.

U.S. Pat. No. 5,863,769 discloses using IL-1 RA for treating various diseases. This prior art patent does not teach the use of an interleukin antagonist or other biologic delivered via the vertebral venous system as described in the present invention to treat disorders of the brain.

U.S. Pat. No. 6,013,253 discloses using interferon and IL-1 RA for treating multiple sclerosis. This prior art patent does not teach the use of an interleukin antagonist or other biologic delivered via the vertebral venous system as described in the present invention to treat disorders of the brain.

U.S. Pat. No. 5,075,222 discloses the use of IL-1 inhibitors for treatment of various disorders. This prior art patent does not teach the use of an interleukin antagonist or other biologic delivered via the vertebral venous system as described in the present invention to treat disorders of the brain.

U.S. Pat. No. 6,159,460 discloses the use of IL-1 inhibitors for treatment of various disorders. This prior art patent does not teach the use of an interleukin antagonist or other biologic delivered via the vertebral venous system as described in the present invention to treat disorders of the brain.

U.S. Pat. No. 6,096,728 discloses the use of IL-1 inhibitors for treatment of various disorders. This prior art patent does not teach the use of an interleukin antagonist or other biologic delivered via the vertebral venous system as described in the present invention to treat disorders of the brain.

U.S. Pat. No. 6,548,527 to Rahman discloses the use of etanercept for the treatment of immune mediated ear disorders. This prior art patent does not teach the use of etanercept or other biologic delivered via the vertebral venous system as described in the present invention to treat disorders of the brain.

US patent application 20040072885 to Rahman discloses the use of etanercept for the treatment of immune mediated ear disorders. This prior art patent does not teach the use of an etanercept or other biologic delivered via the vertebral venous system as described in the present invention to treat disorders of the brain.

An article (Rahman M U, Poe D S, Choi H K. Etanercept therapy for immune-mediated cochleovestibular disorders: preliminary results in a pilot study. Otol Neurotol. 2001 September; 22(5):619-24.) disclosed the use of etanercept by subcutaneous administration for the treatment of immune mediated ear disorders. This prior art patent does not teach the use of etanercept or other biologic delivered via the vertebral venous system as described in the present invention to treat disorders of the brain.

Clemens(reference 57) demonstrated that the internal and external vertebral venous plexuses freely intercommunicate, and this was also demonstrated by Vogelsang (reference 58) with the use of intraosseous spinal venography. But neither Clemens nor Vogelsang discussed the use of the VVS to facilitate delivery of large molecules to the brain, nor did they discuss the use of the VVS for therapeutic purposes.

Groen (reference 50) confirmed the fact that all three divisions of the vertebral venous system (internal and external plexuses, and the basivertebral veins) freely intercommunicated, and that all divisions of this system lacked valves. But Groen did not discuss the use of the VVS to facilitate delivery of large molecules to the brain, nor did he discuss the use of the VVS for therapeutic purposes.

Two recent articles (Lirk references 54 and 55) discuss an anatomic finding, disclosing the existence of a gap in a ligamentous barrier to the epidural space. These articles, however, do not discuss the administration of large molecules by the perispinal route, or the relevance of this anatomic finding to the delivery of large molecules to the brain.

Batson in 1940 (reference 47) published information regarding the vertebral venous system. Experimentally he demonstrated a connection between the pelvic venous system and the vertebral venous system, and proposed that this was a route whereby carcinoma originating in the pelvis could metastasize to the spine. His work did not propose the use of the VVS for therapeutic purposes, nor did it discuss or imply this possiblity. His work did not disclose the methods of the present invention for delivery of large molecules to the brain.

Ruiz and Gisolf (references 44 and 45) have recently published articles discussing the vertebral venous system and its connections to the cranial venous system. Neither authors discuss the potential use of this system as a route of administration of large molecules to the brain.

Retrograde cerebral perfusion has been previously demonstrated to deliver dye to the surface of the brain in pigs after superior vena caval injection (Ye reference 42)) but the authors did not propose the use of this route to deliver large molecules to the brain.

Several authors (references 44-50) have discussed the anatomy and function of the vertebral venous system but none have proposed the use of the vertebral venous system as a route of delivery of large molecules to the brain, nor have they proposed the methods of the present invention.

Two articles by Byrod discussed a mechanism whereby substances applied epidurally can cross into the endoneurial space (Byrod references 51 and 52), but neither article discusses the perispinal use of a large molecule for delivery to the brain.

Robinson (reference 60) states the prevailing view that systemic administration of etanercept does not lead to therapeutic concentrations of etanercept in the brain, because systemically administered etanercept does not cross the BBB.

Markomichelakis (reference 62) in 2005, following the issuance of U.S. Pat. No. 6, 428,787 by this inventor which claimed the use of infliximab to treat macular degeneration, described the regression of macular degeneration following infliximab treatment given systemically. This reference did not describe or discuss the use of perispinal infliximab.

Olmarker has filed patent applications regarding the use of anti-TNF molecules for treatment of spinal disorders, including US20010027175, 20010055594, 20030176332, 20050220791, 20010027199, and 20030039651, which have led to U.S. Pat. Nos. 6,635,250, 6,649,589, and 7,115,557. None of these applications or patents are enabling for the use of perispinal etanercept or perispinal golimumab for the applications discussed in the present invention.

None of the prior art patents disclose or teach the use of perispinal administration of large molecules as in the present invention as a way of delivering large molecules to the brain, the eyes, or the head, in which this method of administration provides the patient with a better opportunity to heal, slows disease progression, treats infection or otherwise improves the patient's health.

None of the prior art patents disclose or teach the use of perispinal administration of golimumab as in the present invention as a way of delivering golimumab to the brain, the eyes, or the head, in which this method of administration provides the patient with a better opportunity to heal, slows disease progression, treats infection or otherwise improves the patient's health.

In addition the prior art does not contain a description of the methods of the current invention to deliver molecules smaller than 2,000 daltons MW to the brain and other structures of the head.

Accordingly, it is an object of the present invention to provide golimumab administered through the perispinal route as a new method of golimumab so that the use of golimumab will improve a patient's health.

Another object of the present invention is to provide a method to deliver golimumab across the blood-brain barrier so that it is delivered to the brain in a therapeutically effective dose and thereby treats a disease or disorder of the brain.

Another object of the present invention is to provide a method to deliver golimumab across the blood-eye barrier so that it is delivered to the eye in a therapeutically effective dose and thereby treats a disease or disorder of the eye.

Another object of the present invention is to provide a method to deliver golimumab across the blood-eye barrier so that it is delivered to the retina in a therapeutically effective dose and thereby treats a disease or disorder of the retina.

Another object of the present invention is to provide a method to deliver golimumab across the blood-eye barrier so that it is delivered to the retina in a therapeutically effective dose and thereby treats macular degeneration.

Another object of the present invention is to provide a method to deliver golimumab across the blood-eye barrier so that it is delivered to the retina in a therapeutically effective dose and thereby treats a disease or disorder of the diabetic retinopathy.

Another object of the present invention is to provide a method to deliver golimumab across the blood-brain barrier so that it is delivered to the auditory apparatus in a therapeutically effective dose and thereby treats a disease or disorder of the auditory apparatus.

Another object of the present invention is to provide a method to deliver golimumab across the blood-brain barrier so that it is delivered to the brain in a therapeutically effective dose and thereby treats dementia.

Another object of the present invention is to provide a method to deliver golimumab across the blood-brain barrier so that it is delivered to the brain in a therapeutically effective dose and thereby treats a brain tumor.

Another object of the present invention is to provide a method to deliver golimumab across the dural barrier so that it is delivered to the spine in a therapeutically effective dose and thereby treats a malignant tumor metastatic to the spine.

Another object of the present invention is to provide a method to deliver golimumab across the dural barrier so that it is delivered to the spinal nerve roots, the spinal cord, the dorsal root ganglia, or the spine in a therapeutically effective dose and thereby treats a spinal disorder, including sciatica, degenerative disc disease, cervical radiculopathy, low back pain, or related conditions.

Accordingly, it is an object of the present invention to provide large molecules administered through the perispinal route as a new method of use of such molecules so that the use of these molecules will improve a patient's health.

Another object of the present invention is to provide a method to deliver a large molecule across the blood-brain barrier so that it is delivered to the brain in a therapeutically effective dose and thereby treats a disease or disorder of the brain.

Another object of the present invention is to provide a method to deliver a large molecule across the blood-eye barrier so that it is delivered to the eye in a therapeutically effective dose and thereby treats a disease or disorder of the eye.

Another object of the present invention is to provide a method to deliver a large molecule across the blood-eye barrier so that it is delivered to the retina in a therapeutically effective dose and thereby treats a disease or disorder of the retina.

Another object of the present invention is to provide a method to deliver a large molecule across the blood-eye barrier so that it is delivered to the retina in a therapeutically effective dose and thereby treats macular degeneration.

Another object of the present invention is to provide a method to deliver a large molecule across the blood-eye barrier so that it is delivered to the retina in a therapeutically effective dose and thereby treats a disease or disorder of the diabetic retinopathy.

Another object of the present invention is to provide a method to deliver a large molecule across the blood-brain barrier so that it is delivered to the auditory apparatus in a therapeutically effective dose and thereby treats a disease or disorder of the auditory apparatus.

Another object of the present invention is to provide a method to deliver a large molecule across the blood-brain barrier so that it is delivered to the brain in a therapeutically effective dose and thereby treats dementia.

Another object of the present invention is to provide a method to deliver a large molecule across the blood-brain barrier so that it is delivered to the brain in a therapeutically effective dose and thereby treats a brain tumor.

Another object of the present invention is to provide a methods to deliver a molecules with a molecular weight less than 2,000 daltons across the blood-brain barrier so that it they are delivered to the brain, the eye, or the auditory apparatus in a therapeutically effective dose.

None of the prior art patents or articles disclose or teach the use of perispinal administration without direct intrathecal injection of etanercept or other large molecules, as in the present invention, as a way of treating a brain, retina, or cranial nerve disorder, in which said large molecule is delivered via the vertebral venous system and provides the patient with a better opportunity to heal, slows disease progression, improves brain or retinal function or otherwise improves the patient's health.

Accordingly, it is an object of the present invention to provide large molecules administered into the perispinal area, outside of the intrathecal space, via the vertebral venous system, as a new method of biologic treatment of neurological conditions of the brain, retina, eye or auditory apparatus such that the use of these large molecules will result in improved health.

Another object of the present invention is to provide large molecules delivered via the vertebral venous system for providing suppression and inhibition of the action of specific cytokines in a human to treat disorders of the brain, retina, cranial nerves, spine, spinal cord, spinal nerve roots, dorsal root ganglia or hearing.

Another object of the present invention is to provide a large molecule delivered via the vertebral venous system so that it is delivered to the brain, retina, cranial nerves, or auditory apparatus in a therapeutically effective dose and thereby improves disorders of the brain, retina, cranial nerves, or hearing.

Another object of the present invention is to provide large molecules that produce biologic effects in patients with vision loss by inhibiting the inflammatory cascade in the human body for the immediate, short term (acute conditions) and long term (chronic conditions), such that these biologic effects will produce clinical improvement in the patient and will give the patient a better opportunity to heal, improve vision, slow vision loss, prevent neurological damage, or otherwise improve the patient's health.

Another object of the present invention to provide a cancer chemotherapeutic agent delivered via the vertebral venous system for the treatment of a malignant disease of the brain in a human such that the use of this cancer chemotherapeutic agent results in decreased or delayed growth of the malignancy.

Another object of the present invention to provide bevacizumab delivered via the vertebral venous system for the treatment of a malignant disease of the brain in a human such that the use of bevacizumab results in decreased or delayed growth of the malignancy.

Another object of the present invention to provide pegaptanib or ranibizumab delivered via the vertebral venous system for the treatment of a malignant disease of the brain in a human such that the use of bevacizumab results in decreased or delayed growth of the malignancy.

Another object of the present invention to provide pegaptanib or ranibizumab delivered via the vertebral venous system for the treatment of ocular neovascularization in a human such that the use of pegaptanib or ranibizumab results in improved vision.

Another object of the present invention to provide pegaptanib or ranibizumab delivered via perispinal administration for the treatment of a malignant disease of the brain in a human such that perispinal administration results in effective delivery of pegaptanib or ranibizumab via the vertebral venous system thereby resulting in decreased or delayed growth of the malignancy.

Another object of the present invention to provide pegaptanib or ranibizumab delivered via perispinal administration for the treatment of ocular neovascularization in a human such that perispinal administration results in effective delivery of pegaptanib or ranibizumab via the vertebral venous system thereby resulting in improved vision.

Another object of the present invention to provide bevacizumab delivered via perispinal administration for the treatment of a malignant disease of the brain in a human such that perispinal administration results in effective delivery of bevacizumab via the vertebral venous system thereby resulting in decreased or delayed growth of the malignancy.

Another object of the present invention to provide a TNF antagonist delivered via the vertebral venous system for the treatment of sensorineural hearing loss in a human such that the use of this antagonist results in improved hearing.

Another object of the present invention to provide a TNF antagonist for the treatment of sensorineural hearing loss in a human such that the use of this antagonist results in improved hearing without the use of a hearing aid, in a manner that is both safe and effective.

Another object of the present invention to provide a TNF antagonist delivered via the vertebral venous system for the treatment of vision loss in a human such that the use of this antagonist results in improved vision without the need for surgery.

Another object of the present invention is to provide novel and improved routes of administration for the selected TNF antagonist so that it enters the vertebral venous system in a therapeutically effective amount for the treatment of macular degeneration in a human such that the use of this antagonist with this method results in improved vision or in delay of disease progression in a manner that is both safe, effective, and economical.

Another object of the present invention is to provide novel and improved routes of administration for the selected biologic so that it enters the vertebral venous system in a therapeutically effective amount for the treatment of a clinical disorder of the brain in a human such that the use of this biologic with this method results in improved health in a manner that is both safe, effective, and economical.

5. SUMMARY OF THE INVENTION

The present invention provides specific methods for delivering golimumab to a mammal utilizing perispinal administration without direct intrathecal injection. For the purposes of this patent "perispinal" is to be considered as referring to "perispinal extrathecal"; therefore direct intrathecal administration is excluded from the methods discussed.

The term "treatment" as used herein in the context of treating a condition, refers generally to the treatment and therapy, whether a human or an animal, in which some desired therapeutic effect is achieved, for example the inhibition of the progression of the condition or illness, and includes the reduction in the rate of progress, a halt in the progression of an illness, amelioration of the adverse condition, and cure of the condition. Treatment as a prophylactic measure, as well as combination treatments and therapies are also included.

As used herein, "therapeutically effective" refers to the material or amount of material which is effective to prevent, alleviate, or ameliorate one or more symptoms or signs of a disease or medical condition, produce clinical improvement, delay clinical deterioration, and/or prolong survival of the subject being treated.

As used herein, "subject" refers to animals, including mammals, such as human beings, domesticated animals, and animals of commercial value.

As used herein, the term "biologic" is defined as a drug which is derived or prepared from the DNA of a living organism, which has a relatively large molecular weight and a high structural complexity as compared with biologically active substances which are produced by chemical synthesis. The living sources from which biologics may be obtained include humans, other animals, and microorganisms. The drug may be produced by recombinant means, or may be extracted and purified directly from the living source.

As used herein, "perispinal administration without direct intrathecal injection" refers to administration adjacent to the spine, but outside of the intrathecal space (extrathecal), wherein the injection needle or catheter does not penetrate the dural barrier. Administration therefore is not directly into the cerebrospinal fluid.

Non-brain capillaries are made up of endothelial cells which are separated by small gaps that allow chemicals in solution to pass into the blood stream, where they can be transported thoughout the body. In non-brain capillaries, compounds having molecular weights greater than 25,000 Daltons can undergo transport. In contrast, endothelial cells in brain capillaries are more tightly packed, due to the existence of zonula occludentes (tight junctions) between them, thereby blocking the passage of most molecules. The blood-brain barrier blocks most molecules except those that cross cell membranes by means of lipid solubility (such as, for example, oxygen, carbon dioxide, and ethanol) and those which are allowed in by specific transport systems (such as, for example, sugars, amino acids, purines, nucleosides and organic acids). Generally, it is accepted that substances having a molecular weight greater than 500 daltons cannot cross the blood-brain barrier, whereas substances having a molecular weight less than 500 daltons can cross the blood-brain barrier.

Because they do not effectively cross the blood-brain barrier, biologics having a molecular weight greater than 500 are not effective when administered systemically. For example, etanercept has a molecular weight of 150,000 Daltons, and is not effective for treating conditions of the brain, eye, spinal chord, and cranial nerves. Thus, utilization of the VVS is particularly useful for the administration of high molecular weight biologics such as bevacizumab or etanercept, for delivery to the brain, retina, eye, cranial nerves, spine and spinal cord, thereby enabling the treatment of a wide range of previously intractable disorders of the brain, the retina, and the nervous system, including those which are inflammatory, malignant, infectious, autoimmune, vascular, and degenerative.

In addition the methods of the present invention may be used to deliver molecules with a MW less than 2,000 daltons to the brain and other structures of the head more efficiently than if delivered systemically, and these methods utilizing these smaller molecules are also to be considered a part of this invention.

Perispinal administration involves anatomically localized delivery performed so as to place golimumab directly in the vicinity of the spine, and thereby facilitate delivery of golimumab to the brain, the eye, the retina, the auditory apparatus, the cranial nerves, the spinal nerve roots, the dorsal root ganglia, the spinal cord or the head. Perispinal administration includes, but is not limited to, the following types of administration: parenteral; subcutaneous; intramuscular; and interspinous; and specifically includes the use of interspinous injection carried through the skin in the midline of the neck or back, directly overlying the spine, so that the large molecule is delivered into the interspinous space. Perispinal administration leads to enhanced delivery of golimumab to the brain, the eye, the retina, the auditory apparatus, the spine and contiguous structures, and the cranial nerves or the head in a therapeutically effective amount, via the vertebral venous system. Delivery of a large molecule to the brain utilizing the methods of the present invention includes the use of the vertebral venous system to deliver the large molecule to the brain via retrograde venous flow. Physical positioning may also be used to enhance delivery via this route.

All of the large molecules available for therapeutic use are approved for systemic administration, either by subcutaneous (SC) or intravenous (IV) administration. None have been approved for perispinal or interspinous administration.

This patent application describes novel methods of administration of large molecules, utilizing perispinal administration, which results in improved efficiency (decreased dose for equivalent therapeutic effect) and/or increased effectiveness (increased therapeutic effect for equivalent therapeutic dose) compared with systemic administration.

This invention is distinguished from the prior art in a variety of ways, including the use and description of novel and useful new uses, methods of use, and concepts involving large molecules, including:

1. Novel uses of perispinal administration to enhance delivery of golimumab and other large molecules to the brain, the eye, the retina, the auditory apparatus, the cranial nerves or the head; and
2. Novel methods of use of large molecules; and
3. Novel concepts, including:
   a. Perispinal (extrathecal) administration distinguished from systemic forms of administration and intrathecal administration;
   b. The use of the vertebral venous system to deliver golimumab and other large molecules to the brain, the eye, the retina, the auditory apparatus, the cranial nerves, the spinal nerve roots, the dorsal root ganglia, the spinal cord or the head;
   c. The use of physical maneuvers to facilitate delivery of golimumab to the brain, the eye, the retina, the auditory apparatus, the cranial nerves or the head;
   d. The use of physical positioning to influence the direction of venous flow within the vertebral venous system and thereby deliver therapeutic molecules to the brain, the eye, the retina, the auditory apparatus, the cranial nerves or the head;
   e. The use of retrograde venous perfusion to deliver therapeutic molecules to the brain, the eye, the retina, the auditory apparatus, the cranial nerves or the head;
   f. The use of retrograde venous perfusion via the vertebral venous system to facilitate delivery of therapeutic molecules to the brain, the eye, the retina, the auditory apparatus, the cranial nerves or the head;
   g. The use of the vertebral venous system as a "back door" to facilitate delivery of therapeutic molecules to the brain, the eye, the retina, the auditory apparatus, the cranial nerves or the head;
   h. The use of perispinal administration to introduce a large molecule into the vertebral venous system;
   i. The use of perispinal administration to efficiently deliver large molecules to the brain, the eye, the retina, the auditory apparatus, the cranial nerves, the spinal nerve roots, the dorsal root ganglia, the spinal cord or the head.

The same methods described for golimumab of this invention also apply to other large molecules, such as etanercept, certolizumab pegol, IL-1 Trap, Kineret®, bevacizumab, pegaptanib, ranibizumab, rituximab, Zevalin®, Mylotarg®, Campath®, HumaSpect®, abatacept, cetuximab, panitumumab, pegfilgrastim, filgrastim, erythropoietin, Aranesp®, trastuzumab, Pegasysg®, Intron A®, PEG-Intron®, Infergen®, Avonex®, Rebif®, Betaseron®, Actimmune®, Ontak®, Simulect®, Zenapax®, Genkaxin®, recombinant human growth hormone, reteplase, alteplase, tPA (tissue plasminogen activator), urokinase plasminogen activator, streptokinase, urokinase, or immune globulin), and smaller molecules, such as Tarceva®, all of which maybe given by perispinal administration, and whose use, by perispinal administration without direct intrathecal injection, constitute part of this invention.

6. DETAILED DESCRIPTION OF THE PREFERRED EMBODIMENTS

The use of perispinal administration of cytokine antagonists to treat neurological disorders is discussed in US patent application 20030049256 of this inventor. The use of perispinal administration without direct intrathecal injection and the vertebral venous system to deliver large molecules to the brain, the eye, and the auditory apparatus are discussed in the following provisional patent applications:
60/585,735 filed Jul. 6, 2004;
60/659,414 filed Mar. 9, 2005;
60/662,744 filed Mar. 17, 2005;
and 60/669,022, filed Apr. 7, 2005, This is a continuation-in-part of U.S. patent application Ser. No. 11/016,047, filed Dec. 18, 2004, entitled "Methods of use of etanercept to improve human cognitive function", which is a continuation-in-part of U.S. Patent Application 20030049256, also known as U.S. patent application Ser. No. 10/269,745, entitled "Cytokine antagonists for neurological and neuropsychiatric disorders", filed Oct. 9, 2002, now U.S. Pat. No. 6,982,089, which is a continuation-in-part of Ser. No. 10/236,097, filed on Sep. 6, 2002, now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S.

Pat. No. 6,015,557, which is a continuation-in-part of application Ser. No. 09/256,388, filed on Feb. 24, 1999, now abandoned. This application is also related to provisional U.S. patent application 60/662,744 entitled "Methods of Use of the Vertebral Venous System to Deliver Biologics to the CNS" filed Mar. 16, 2005. The use of perispinal administration of cytokine antagonists to treat neurological disorders is discussed in US patent application 20030049256 of this inventor. The use of perispinal administration without direct intrathecal injection and the vertebral venous system to deliver large molecules to the brain, the eye, and the auditory apparatus are discussed in provisional patent applications 60/585,735 filed Jul. 6, 2004; 60/659,414 filed Mar. 9, 2005; 60/662,744 filed Mar. 17, 2005; and 60/669,022, filed Apr. 7, 2005. In addition this provisional patent application is related to U.S. provisional patent application entitled "Methods to facilitate transmission of golimumab and other therapeutic molecules across the blood-brain-barrier" filed with the USPTO on Nov. 18, 2005.

All of the above patents and patent applications enumerated in the above three paragraphs are incorporated by reference in their entirety herein.

Perispinal administration of a molecule when compared to systemic administration, carries with it one or more of the following advantages for the present invention:
1) greatly improved efficacy due to improved delivery of the therapeutic molecule to the brain, the eye, the retina, the auditory apparatus, the cranial nerves, the spinal nerve roots, the dorsal root ganglia, the spinal cord or the head via the vertebral venous system (VVS).
2) greater efficacy due to the achievement of higher local concentration in the interspinous space, leading to improved delivery to the VVS and the brain, the eye, the retina, the auditory apparatus, the cranial nerves, the spinal nerve roots, the dorsal root ganglia, the spinal cord or the head.
3) greater efficacy due to the ability of the administered therapeutic molecule to reach the brain, the eye, the retina, the auditory apparatus, the cranial nerves, the spinal nerve roots, the dorsal root ganglia, the spinal cord or the head without degradation caused by hepatic or systemic circulation;
4) more rapid onset of action;
5) longer duration of action; and
6) Potentially fewer side effects, due to lower required dosage.

These advantages apply to both large molecules, such as monoclonal antibodies, which typically have a MW of more than 100,000 daltons, and to smaller molecules, many of which, even though they have a MW less than 2,000 daltons, have difficulty traversing the BBB. Even smaller molecules, those with a MW less than 500 daltons, which often can cross the BBB, will achieve a greater therapeutic concentration in brain or eye tissue if administered by perispinal delivery without direct intrathecal injection, especially if immediately following injection the postural adjustments are made to direct the head downward with the body in a Trendelenburg position, thereby facilitating retrograde venous perfusion via the intracranial anastomoses of the vertebral venous system. The blood-eye barrier, for the purposes of this patent, will be traversed by the methods of the present invention in a manner equivalent to the manner in which these molecules cross the blood-brain barrier. The blood-nerve barrier protecting the spinal nerve roots and the spinal cord, consisting in large part of the barrier formed by the dura mater, will also be traversed in a manner utilizing the methods of the present invention i.e. by carriage in the vertebral venous system, etc.

The inventor has extensive clinical experience utilizing perispinal injection of etanercept for the treatment of disc-related pain and radiculopathy, including low back pain, neck pain, lumbar radiculopathy (sciatica), cervical radiculopathy, pain associated with annular tear of the intervertebral disc, and pain associated with degenerative disc disease (see Tobinick reference 63) (Tobinick, E. and S. Davoodifar, *Efficacy of etanercept delivered by perispinal administration for chronic back and/or neck disc-related pain: a study of clinical observations in* 143 *patients*. Curr Med Res Opin, 2004. 20(7): p. 1075-85). In this article the inventor reported the results of perispinal etanercept treatment for 143 patients, including those with disc bulge, protrusion, extrusion or herniation; lumbar and cervical radiculopathy; degenerative disc disease; central spinal stenosis; spondylolisthesis; back pain, neck pain, or sciatica; and annular tear of the intervertebral disc. The 143 patients had a mean duration of pain of 9.8 years. After a mean of 2.3 doses of perispinal etanercept the mean VAS intensity of pain, sensory disturbance, and weakness was significantly reduced at 20 min., 1 day, 1 week, 2 weeks, and 1 month. In a previous publication (Tobinick, E. L. and S. Britschgi-Davoodifar, *Perispinal TNF-alpha inhibition for discogenic pain*. Swiss Med Wkly, 2003. 133(11-12): p. 170-7) the inventor documented clinical improvement following perispinal etanercept in a cohort of 20 patients with the following diagnoses: acute lumbar radiculopathy; chronic cervical and lumbar discogenic pain; subacute lumbar radiculopathy; chronic discogenic pain and failed back surgery syndrome; chronic low back pain and sciatica; chronic, treatment-resistant discogenic pain. Rapid, substantial, and sustained clinical pain reduction and improvement in functional disability was documented in this group of patients for a mean of 230 days. At the time that these articles were published the inventor was not aware of the fact that the vertebral venous system drains the perispinal area, including both the deeper interspinous space superficial to the ligamentum flavum and the subcutaneous perispinal space which overlies the spinous processes and the deeper interspinous space. It is a method of the present invention to introduce large molecules into this area (the perispinal area) to enable them to drain into the vertebral venous system and thereby cross the blood-nerve barrier and produce therapeutic benefit for treating the spinal conditions enumerated in this paragraph. This may be accomplished by perispinal injection of these molecules, which leads to entry of the large molecules into the vertebral venous system, and then delivery of these molecules, by retrograde venous flow due to lack of venous valves in the VVS, to the spinal nerve roots, the dorsal root ganglia, and the spinal cord. In the case of etanercept and golimumab, for example, this results in neutralization of excess TNF and clinical improvement in patients suffering from a variety of spinal ailments, including specifically those enumerated in this paragraph. The dosage needed to accomplish this is outlined in the above articles (references 63 and 64) and elsewhere in this patent application with respect to etanercept. For golimumab, the dosage used will vary between 10 and 100 mg, including a dosage of 25 mg or 50 mg given as a perispinal extrathecal injection.

The inventor has successful clinical experience with perispinal administration of etanercept, a large molecule (MW 149,000 daltons) for the treatment of Alzheimer's Disease(AD) (see experimental results infra) which illustrates the clinical efficacy of this method of delivery of large molecules for the treatment of brain disorders, and, specifically, the ability of this delivery method to enable etanercept to cross the BBB and effectively treat AD. It should be noted that a previous clinical trial utilizing etanercept (reference 61)

delivered systemically (by subcutaneous administration remote from the spine) failed to show efficacy, thereby providing prima facie evidence of the superiority of perispinal administration to deliver etanercept to the brain, when a comparison of the failed trial results to the successful experimental results obtained utilizing perispinal administration of etanercept, detailed infra, is made. The methods described herein involve the use of perispinal administration to effectively deliver large molecules to the brain, the eye, the retina, the auditory apparatus, the cranial nerves or the head, for therapeutic use in humans and other mammals.

The VVS consists of an interconnected and richly anastomosed system of veins which run along the entire length of the vertebral canal. The vertebral venous plexus, for descriptive purposes, has been separated into three intercommunicating divisions: the internal vertebral venous plexuses (anterior and posterior) lying within the spinal canal, but external to the dura; the external vertebral venous plexuses (anterior and posterior) which surround the vertebral column; and the basivertebral veins which run horizontally within the vertebrae. Both the internal and external vertebral venous plexus course longitudinally along the entire length of the spine, from the sacrum to the cranial vault. Utilizing corrosion casting and injections of Araldite, Clemens demonstrated that the internal and external vertebral venous plexuses freely intercommunicate, and this was also demonstrated by Vogelsang with the use of intraosseous spinal venography. Groen and his colleagues with an improved Araldite injection technique which utilized thrombolytics, confirmed the fact that all three divisions of the vertebral venous system (internal and external plexuses, and the basivertebral veins) freely intercommunicated, and that all divisions of this system lacked valves. The internal vertebral venous plexus communicates with the intraspinal and radicular veins and freely communicates with the external vertebral venous plexus via the intervertebral veins (see references 44-50). In addition, the VVS communicates with the azygous veins, and has other connections to the caval venous system, but not efficiently. Therefore a conventional intravenous injection in the antecubital fossa, for example, or into one of the large veins of the forearm, which delivers a solution containing a given therapeutic molecule into the caval venous system, does not efficiently deliver the same therapeutic molecule to the VVS. Likewise, delivery of a solution containing a given therapeutic molecule by perispinal administration will not result in efficient delivery of the given therapeutic molecule into the caval venous system, but will result in efficient delivery into the VVS. The caval venous system and the VVS are separate and largely independent (see reference 59), although they are interconnected, although not in an efficent manner. To phrase the same thoughts in a different way, it would be accurate to say that perispinal administration of a large molecule will result in efficient delivery of the large molecule to the VVS, with only a small amount of delivery of the large molecule into the caval venous system. Delivery of the same large molecule by intravenous infusion into an arm vein, for example, will deliver the large molecule to the caval venous system, expose the large molecule to dilution throughout the body, and fail to deliver the large molecule to the brain, the eye, the retina, the auditory apparatus, the cranial nerves or the head.

A specific anatomic route, by which a large molecule delivered by perispinal administration reaches the brain, has been defined by the inventor. This route is as follows. A large molecule is delivered to the interspinous space in proximity to the ligamentum flavum by percutaneous injection through the skin by midline interspinous needle injection. Large molecules delivered to the interspinous space in this way (being the anatomic region in the midline of the back, in-between two adjacent spinous processes) are delivered into the VVS because the VVS serves to provide venous drainage to the interspinous space and subcutaneous space which is posterior to the spine (see Batson references 48 and 49 for a discussion of the VVS, which, however, does not discuss the therapeutic potential of the VVS). Solutions injected into this area, therefore, will be preferentially absorbed into the VVS rather than into the caval venous system. In addition, a more direct route to the epidural space is also possible for solutions injected into the interspinous space, by travel through midline defects in the ligamentum flavum. Midline defects in the ligamentum flavum are common, particularly in the cervical region. When present the midline ligamentum flavum defect provides a direct route of access for large molecules to the epidural space. Within the epidural space lies a richly interconnected venous plexus (which is part of the VVS), which is valveless and which is capable of transporting large molecules rapidly in the cephalad or caudad directions (see Batson references 48 and 49). Flow within the VVS is bidirectional. Therefore large molecules injected into the interspinous space drain directly into the VVS and thereby gain direct access to the brain, if the patient is positioned properly immediately following injection so that gravity is used to direct flow via the VVS toward the brain. This is possible because the flow within the VVS can be bidirectional; therefore these veins serve not only to drain blood from the brain, but also to deliver venous blood to the brain, in retrograde fashion, via the venous connections of the VVS with the intracranial venous system, including the dural sinuses. This retrograde flow is made possible by the lack of venous valves in the VVS. Retrograde venous delivery of large molecules to the brain is a method of the present invention and a discovery of the inventor. The author has detailed much of his current thinking regarding the vertebral venous system and its connection with the cerebral venous system in a recently published article entitled "The Cerebrospinal Venous System: Anatomy, Physiology, and Clinical Implications" published in Medscape General Medicine in February 2006 (MedGenMed. 2006 February 22;8(1):53.) This article is incorporated in its entirety in this patent application by reference.

The VVS can be used to deliver large biologic therapeutic agents (i.e., biologics having a molecular weight greater than 600 Daltons, preferably greater than 2000 Daltons) utilizing retrograde venous flow from the VVS into the cranial venous sinuses and the intracranial venous system for delivery to the cerebral cortex, eye, retina, spine, cerebellum, brainstem, eighth cranial nerve, cochlea, inner ear, cerebrospinal fluid, spine, spinal cord, dorsal root ganglion, spinal nerve roots, reproductive organs and spinal nerve roots of a subject. Exemplary pharmaceutically acceptable therapeutic agents may include pharmacologic agents, cytokine antagonists and growth factors which can affect neuronal function or the immune response impacting neuronal function, including, but not limited to, for example, golimumab, CDP 870, and etanercept.

Retrograde venous delivery of large molecules to the brain is facilitated by body positioning after interspinous injection. For example, if following cervical interspinous injection the patient is placed in the head down trendelenburg position then the inventor has discovered that this will lead to effective delivery of the large molecule to the brain, via retrograde flow in the VVS into the cranial venous system.

The inventor is using the vertebral venous system in a non-obvious way for the inventions disclosed herein. For a venous system is routinely conceptualized as a system that drains blood from a target area or organ. For example the venous system which drains the kidneys is widely acknowledged to be a vascular system that drains blood from the kidneys, not as a way of delivering a therapeutic molecule to the kidneys. Likewise the venous system of the brain is widely medically recognized as a system which functions to drain blood from the brain. It would be counter-intuitive to propose using the VVS to deliver a therapeutic molecule to the brain, by conventional thinking. Likewise the use of the vertebral venous system to achieve delivery of therapeutic compounds to the brain is not obvious, because conventional thinking is that this venous system functions to drain venous blood away from these anatomic sites. Therefore the inventions of consideration here are in this way counter-intuitive, because they rely on the vertebral venous system to deliver therapeutic molecules (including specifically large molecules) to the brain, the eye, the retina, the auditory apparatus, the cranial nerves or the head. This delivery is accomplished by retrograde venous flow (opposite from the usual direction), which is made possible by the lack of valves in this venous system, and by the proper use of gravity and positioning of the patient so that venous flow in the desired direction is accomplished. The rich connections between the cranial venous system and the vertebral venous system were beautifully depicted in 1828 by Breschet (reference 56), but this anatomic route remains largely unrecognized by the medical community till the present time.

Correct positioning of the patient so as to facilitate retrograde flow in the desired direction is utilized as part of the present invention to achieve improved delivery of golimumab and other large molecules to the brain, the eye, the retina, the auditory apparatus, the cranial nerves or the head from its injection point. Since the target is delivery of the large molecule to the brain, the eye, the retina, the auditory apparatus, the cranial nerves or the head, positioning following delivery utilizing head-down trendelenburg positioning, assists in delivering the large molecule to the target. In most cases, for delivery of a large molecule to the brain, the eye, the retina, the auditory apparatus, the cranial nerves or the head, interspinous injection is peformed overlying the posterior aspect of the cervical spine, in the interspinous region between the C4 and C8 spinal processes, followed by placement of the patient in the head-down trendelenburg position, usually in the prone position, if possible, since the large molecule is delivered, as described, to an area dorsal to the spine.

Batson's plexus may be used to introduce a variety of therapeutic molecules to the brain, retina, cranial nerves, and head via retrograde venous flow from Batson's plexus into the cranial venous sinuses and the intracranial venous system. This method bypasses the well known barrier which prevents large molecules introduced into the systemic circulation from reaching the brain (the BBB). The BBB prevents molecules larger than approximately 600 daltons from entering the brain via the systemic circulation. Virtually all biopharmaceuticals are larger than this. For example, etanercept has a molecular weight of 149,000 daltons, and insulin has a MW of 5,000 (compared with water which has a MW of 18). This method is particularly useful, therefore, for the administration of biologics, such as etanercept, erythropoietin, GM-CSF, ranibizumab, etc., whose size when delivered systemically prevents their efficient passage into the brain, retina, eye, and cranial nerves, but whose potency, because of their biologic origin, is extremely high. Effective delivery of these molecules to the brain, the retina, the eye, and the cranial nerves using the methods of the present invention thereby enables the treatment of a wide range of previously intractable disorders of the brain, the retina, and the nervous system, including those which are inflammatory; malignant; infectious; autoimmune; vascular; and degenerative.

The vertebral venous system is both anatomically and physiologically distinct from the venous system which drains the abdomen and thorax, which has been designated by others as the intracavitary venous system, with the vertebral venous system designated as the extracavitary venous system. Other nomenclature for the VVS also comes to mind, such as the valveless venous system, or the bi-directional venous system, but they are perhaps less suitable than the VVS. The VVS and the intracavitary venous system also share anastomoses, as has been discussed at length by Batson. Batson has also described the retrograde flow possible with the VVS, but has not proposed the possible use of the VVS as a route to deliver therapeutic compounds, nor has anyone else. Again, this retrograde route of delivery is uniquely possible utilizing the VVS because of the lack of venous valves.

Use of the vertebral venous system as a route to deliver golimumab to the retina, eye or optic nerve via retrograde venous flow is a novel new delivery method for treating disorders of the brain, retina, eye or optic nerve.

This method allows the treatment of inflammatory or degenerative disorders of the retina and/or optic nerve, such as macular degeneration, diabetic retinopathy, glaucoma and retinitis pigmentosa, which involve excessive levels of TNF or which are mediated by VEGF. Excess TNF appears to have a direct deleterious effect on vision, and etanercept, delivered via the vertebral venous system, appears to have the ability to ameliorate this adverse effect. Perispinal administration of these biologics enables the biologic to reach the internal contents of the eye, including the choroidal vasculature and the retina, in therapeutic amounts, via retrograde flow within the cranio-vertebral venous system.

The methods of the present invention include the perispinal administration of the biologics of consideration herein (listed below), which can be accomplished in various ways, including transcutaneous interspinous injection, or catheter delivery into the epidural or interspinous space, which results in the biologics being delivered into the vertebral venous system and thence into the brain, retina, cranial nerves, and auditory apparatus in a therapeutic amount.

As defined herein, the auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids.

Midline interspinous administration of etanercept has been demonstrated (see below) to produce improvement in hearing to individuals with certain forms of non-conductive hearing loss. In addition to percutaneous injection into the interspinous space, etanercept may also be delivered to the interspinous or epidural space by implantable catheter, with the catheter reservoir placed remotely, such as in the abdominal area.

The inventor first described improvement in hearing in a 73 y.o. patient after perispinal administration of etanercept for the treatment of sciatica in U.S. Pat. No. 6,423,321. The anatomic route which enables the efficient delivery of perispinal etanercept to the brain is identified by the inventor, and physical maneuvers to facilitate this process are described herein. For the purposes of this patent perispinal etanercept is distinguished from the use of etanercept delivered by subcutaneous administration at anatomic sites, such as the abdomen, thighs, and arms, which are remote from the spine.

Bevacizumab (Avastin™, Genentech) is a recombinant humanized monoclonal IgG1 antibody that binds to and inhibits the biologic activity of human vascular endothelial growth factor (VEGF) and which may be useful for the treatment of retinal disorders which involve neovascularization. Bevacizumab has a molecular weight of 149,000 daltons and is therefore too large to readily cross the blood-brain barrier if administered systemically. Administration of bevacizumab via the vertebral venous system bypasses the blood-brain barrier and allows a therapeutic dose of bevacizumab to reach the retina, therefore enabling the treatment of retinal disorders which involve neovascularization, including macular degeneration and diabetic retinopathy. For this purpose bevacizumab may be administered via perispinal administration, thereby providing access of this monoclonal antibody to the VVS and therefore to the retina.

Pegaptanib and ranibizumab are two biologics which are antagonists of human vascular endothelial growth factor (VEGF) and which may be useful for the treatment of retinal disorders which involve neovascularization. Pegaptanib is a VEGF-neutralizing oligonucleotide aptamer which binds and sequesters VEGF, thereby preventing VEGF receptor activation. Ranibizumab is a recombinant humanized monoclonal antibody fragment with specificity for VEGF. Both pegaptanib and ranibizumab are too large to readily cross the blood-brain barrier or the blood-ocular barrier if administered systemically. They have both shown some efficacy in treating ocular neovasculariztion when administered by injection into the eye by the intravitreal route. Administration of these agents via the vertebral venous system bypasses the blood-brain barrier and the blood-ocular barrier and allows a therapeutic dose to reach the retina, therefore enabling the treatment of retinal disorders which involve neovascularization, including macular degeneration and diabetic retinopathy, without the necessity for intravitreal injection. For this purpose pegaptanib and ranibizumab may be administered via perispinal administration, thereby providing access of biologics to the VVS and therefore to the retina, the choroidal vessels, and the eye without requiring intravitreal injection. Additionally perispinal injection of these two biologics will enable effective delivery of these agents to the brain, thereby allowing the use of these agents for brain tumors and other clinical disorders which will respond positively to modulation of VEGF.

Perispinal administration for delivery of neuroactive molecules other than etanercept, including biologics, cytokines, anti-cytokines, hormones or drugs via the vertebral venous system, in a manner similar to that outlined herein, may be performed. The neuroactive compounds include the individual interleukins IL-1, IL-2, IL-4, IL-6, IL-10, or IL-13; interleukin 1 antagonists, such as IL-1 RA (Kineret®, Amgen) and IL-1 Trap; fusion proteins, such as IL-10 fusion protein or etanercept (Enbrel®, Immunex); other TNF antagonists, including certolizumab pegol, soluble TNF receptor type I or pegylated soluble TNF receptor type 1; human growth hormone and related biologics (recombinant human growth hormone, Humatrope® (somatropin) Eli Lilly & Co., Nutropin®/NutropinAQ® (somatropin), Geref® (sermorelin) Serono, and Protropin® (somatrem) Genentech)); BDNF; erythropoietin (Epogen® (epoetin alpha) Amgen, Procrit® (epoetin alpha) Johnson & Johnson); G-CSF (Neupogen® (filgrastim), Amgen); GM-CSF; Intron® A (interferon alfa-2b) Schering-Plough; Avonex® (interferon beta-1a) Biogen; Alefacept (LFA-3/IgG1 human fusion protein, Amevive® Biogen); Epidermal growth factor; anti-EGF (ABX-EGF, Abgenix); transforming growth factor-beta 1 (TGF-beta 1); NGF; bevacizumab (Avastin™, Genentech); Copaxone® (glatiramer acetate), pegaptanib or ranibizumab as discussed above; or other compounds with CNS, immune, or vascular therapeutic activity.

In particular this invention involves the perispinal administration of golimumab. Golimumab is currently in clinical development by Centocor/Schering-Plough for treatment of rheumatoid arthritis, with potential applications for uveitis, asthma, and Crohn's Disease. It may be described as a immunoglobulin G1, anti-(human tumor necrosis factor α) (human monoclonal CNTO 148 γ1-chain), disulfide with human monoclonal CNTO 148 κ-chain), dimer, and has CAS Registry number 476181-74-5. It is a fully human anti-TNF monoclonal antibody.

This invention involves the use of the above molecules delivered via the vertebral venous system either alone, as monotherapy, or combined with the use of other therapeutics delivered orally or otherwise for treatment of the conditions of consideration herein. For example, the inventor has demonstrated improvement in cognitive function in individuals with MCI or AD treated with either perispinal etanercept alone, or perispinal etanercept in combination with memantine and/or a cholinesterase inhibitor (chosen from the group of donepezil, rivastigmine or galantamine).

A biologic delivered via the vertebral venous system to the retina and the eye after perispinal administration is specifically included as an invention of the current patent.

The methods of the present invention are also distinguished from direct intrathecal administration of large molecules.

The large molecules of the current invention include, but are not limited to, the following:

a. Colony-stimulating factors (including G-CSF, such as filgrastim, pegfilgrastim, and lenograstim; GM-CSF, including, but not limited to sargramostim and molgramostim; Erythroid growth factors, including, but not limited to: recombinant erythropoietin (EPO): epoetin alpha, darbepoetin alpha; and others.

b. TNF antagonists with a molecular weight greater than or equal to 2,000 daltons, including, but not limited to: golimumab, etanercept, infliximab, certolizumab (CDP 870, Cimzia®), CDP 571, onercept, pegylated soluble TNF receptor type I, soluble TNF receptor type I.

c. Interferons, interferon antagonists, and interferon fusion proteins, including, but not limited to: IL-1 Trap; Interferon alfa-2a, rDNA [Interferon alfa-2a - Roferon A; Interferon, alpha-2a, recombinant]; Interferon alfa-2a, rDNA, PEG-[Peginterferon alfa-2a-Pegasys; interferon alpha-2a, recombinant, pegylated]; Interferon alfa-2b, rDNA [Interferon alfa-2-Intron A; Interferon, alpha-2b, recombinant]; Interferon alfa-2b, rDNA, PEG-[Peginterferon alfa-2b-PEG-Intron Powder; interferon alpha-2b, recombinant, pegylated]; Interferon alfa, rDNA/BioPartners [Interferon alpha, recombinant]; Interferon alfacon-1, rDNA [Interferon alfacon-1-Infergen; consensus interferon, recombinant]; Interferon beta-1a, rDNA/Biogen [Interferon beta-1a-Avonex [recombinant]]; Interferon beta-1a, rDNA/Serono [Interferon beta-1a-Rebif [recombinant]]; Interferon betaser, rDNA/Berlex [Interferon beta-1b-Betaseron] (Betaseron has a MW of 18500 daltons); 2-166-Interferon betal (human fibroblast reduced), 17-L-serine-; interferon betaser, recombinant]; Interferon gamma, rDNA [Interferon gamma-1b-Actimmune; [recombinant]]; Interleukin-1ra, rDNA [Anakinra-Kineret; interleukin-1 receptor antagonist; IL-1i]; Interleukin-2, rDNA [Aldesleukin-Proleukin; des-alanyl-1, serine-125 interleukin-2, recombinant; IL-2]; Interleukin-2/diphtheria toxin, rDNA [Denileukin diftitox-ONTAK; Interleukin-2 Fusion Protein; DAB389IL-2; interleukin-2/diphtheria toxin fusion protein, recombinant]; MRA(Roche, Chugai), a humanized anti-IL-6 receptor monoclonal antibody; Interleukin-2 receptor Mab, rDNA/Novartis [Basiliximab-Simulect; Interleukin-2 alpha receptor monoclonal antibody, recombinant]; Interleukin-2 receptor Mab, rDNA/Roche [Daclizumab-Zenapax; Interleukin-2 alpha receptor monoclonal antibody, recombinant]; Interleukin-11, rDNA [Oprelvekin-Neumega; des-Pro Interleukin-11, recombinant; des-Pro IL-11]; IL-6; IL-12; anti-IL-6; and anti-IL-12. As a general rule, interferons have molecular weights ranging from 15,000 to 21,000 daltons.
  d. Antibiotics with a molecular weight of 2,000 daltons or greater;
  e. Cancer chemotherapeutic agents, with a molecular weight greater than or equal to 2,000, including those from the following classes:
    i. Monoclonal antibodies(mAb): including, but not limited to:
      1. Rituximab, a chimeric murine mAb against the CD20 antigen on B-lymphoma cells.
      2. Epratuzumab, a humanized mouse anti-CD22 mAb.
      3. Alemtuzumab, a humanized mAb against CD 52 on B and T lymphoma cells.
      4. Natalizumab, a humanized mAb against the alpha4 subunit of the alpha4Beta1 and Beta 7 integrins.
    ii. Conjugates: Monoclonal antibody-drug, -toxin, or -radionuclide conjugates. These antibodies recognize specific antigenic determinants on malignant cells and their conjugates provide selective toxicity to those cells. A monoclonal antibody conjugate, for the purpose of this invention, is defined as a monoclonal antibody which is conjugated to either a drug, a toxin (such as diptheria toxin) or a radionuclide. These conjugates are particularly suited to perispinal administration, since they are extremely effective, even at low concentration, due to their biologic origin, and can be effectively delivered to the brain or to a brain tumor or lymphoma via the VVS by retrograde venous delivery into the brain. Therefore this class of therapeutic is effective for treating malignant tumors of the brain, either primary, such as glioblastoma multiforme, or metastatic, and for treating CNS lymphomas. These agents include yttrium-90 ibritummomab tiuxetan (Zevalin®) and iodine-131 tositumomab (Bexxar®) which are both murine mAbs against CD20 antigen that are conjugated to a radioactive source and thus selectively deliver radiation to tumors expressing the CD20 antigen (primarily expressed on B-lymphomas).

The above methods detailed for large molecules may be used identically for molecules with a MW of less than 2,000 daltons. The rationale for doing this is that many of these molecules, despite their smaller size, still have difficulty traversing the blood-brain barrier if administered systemically; or perispinal delivery without direct intrathecal injection results in more efficient delivery of these smaller molecules to the brain, the eye, or the auditory apparatus than does systemic or oral delivery. Perispinal administration and delivery to the brain, the eye, or other structures of the head thereby has the advantage of more efficient delivery across the BBB. For example the taxanes, which include paclitaxel (Taxol®) and docetaxel (Taxotere®) have very low BBB penetration when given systemically, despite their respective MW of 854 and 862. Doxorubicin has poor BBB penetration when given systemically despite its MW of 544. Methotrexate and Amphotericin B have poor BBB penetration when given systemically, despite a MW of 454 and 924, respectively, and are often administered intrathecally for CNS use. The perispinal extrathecal methods of the present invention are distinguished from direct intrathecal injection.

With respect to the small molecules of the present invention, they may be categorized as follows:
  1. Cancer chemotherapeutic agents, with a molecular weight less than 2,000, including, but not limited to those from the following classes: (Clinical use: treatment of tumors of the central nervous system or the orbit utilizing perispinal administration without direct intrathecal injection of the following):
    i. Alkaloids: vincristine, vinblastine, vindesine, paclitaxel (Taxol®), docetaxel, etoposide, teniposide.
    ii. Alkylating agents: nitrogen mustards, nitrosureas, cyclophosphamide, thiotepa, mitomycin C, dacarbazine.
    iii. Antibiotics: Actinomycin D, daunorubicin, doxorubicin, idarubicin, mitoxanthrone, bleomycin, mithramycin.
    iv. Antimetabolites: methotrexate, 6-mercaptopurine, pentostatin, 5-fluorouracil, cytosine arabinoside, fludarabine, 2-CDA.
    v. Platinum compounds: Cisplatin.
    vi. Others: tamoxifen (MW 563), flutamide (MW 276), anastrozole (MW 293), gefitinib (Iressa®) and erlotinib (Tarceva®) (MW 429).
  2. Antibiotics: (Clinical use: treatment of bacterial infections of the central nervous system or the eye utilizing perispinal administration without direct intrathecal injection of the following): including, but not limited to cephalosporins, tetracyclines, macrolides, fluroquinolones.
  3. Antivirals: (Clinical use: treatment of viral infections of the central nervous system, particularly meningitis or encephalitis or the eye utilizing perispinal administration without direct intrathecal injection of the following): including, but not limited to oseltamivir, zanamivir, amantadine, anti-HIV drugs, anti-herpes drugs (including acyclovir, famciclovir, valacyclovir), anti-CMV drugs (cidofovir, foscarnet, ganciclovir) and ribavirin.
  4. Antifungal agents: (Clinical use: treatment of fungal infections of the central nervous system or the eye utilizing perispinal administration without direct intrathecal injection of the following): Amphotericin B and its congeners.
  5. Anti-parkinson drugs: (Clinical use: treatment of Parkinson's Disease utilizing perispinal administration without direct intrathecal injection of the following): including, but not limited to levodopa, carbidopa, bromocriptine, selegiline, and dopamine.
  6. Anti-psychotic agents: (Clinical use: treatment of psychoses, including schizophrenia, utilizing perispinal administration without direct intrathecal injection of the following): haloperidol, Prolixin®, Moban®, Loxitane®, Serentil®, Trilafon®, Clozaril®, Geodon®, Risperdal®, Seroquel®, and Zyprexa®.
  7. Antidepressants: (Clinical use: treatment of depression, including for acute depression as a substitute for electroconvulsive therapy), utilizing perispinal administration without direct intrathecal injection of the following): including, but not limited to tricyclics, tetracyclics, trazadone, and SSRIs.
  8. Anticonvulsants: (Clinical use: treatment of seizures, particularly status epilepticus, utilizing perispinal administration without direct intrathecal injection of the following. In addition, please note that these antiepileptic drugs may also be used for treatment of other CNS disorders, such as psychoses and depression): including, but not limited to, Valium®, phenytoin, other hydantoins, barbiturates, gabapentin, lamotrigine, carbamazepine, topiramate, valproic acid, and zonisamide.

9. Opiates and opioids: (Clinical use: treatment of pain, including acute pain (e.g. labor and delivery, or field use following automobile accident, etc.; or chronic pain, as a substitute for chronic intrathecal drug delivery (e.g. as a substitute for chronic intrathecal morphine utilizing an implanted pump), or as a substitute for methadone maintenance treatment), utilizing perispinal administration without direct intrathecal injection of the following): including, but not limited to morphine, oxycodone, other opiates and opioids, including oxycontin and methadone.

Perispinal extrathecal administration is distinguished from intrathecal administration because extrathecal administration is both safer (no dural puncture, therefore no risk of CSF leak; less risk of hemorrhage; no risk of spinal cord traumatic injury; less risk of hemorrhage and infection) and is more effective at delivering the therapeutic molecule into the VVS. The dural barrier, once crossed, will contain the therapeutic molecule within the CSF. CSF flow from the spinal cord to the brain is slow. In contrast retrograde flow to the brain via the VVS is much more rapid.

For the purposes of this discussion, "perispinal" means in the anatomic vicinity of the spine, but outside of the intrathecal space. For this discussion "anatomic vicinity" is generally defined as within 10 centimeters, or functionally defined as in close enough anatomic proximity to allow the therapeutic molecules of consideration herein to reach therapeutic concentration when administered directly to this area without necessitating direct intrathecal delivery.

Perispinal administration for delivery of large molecules, including biologics, cytokines, anti-cytokines, hormones or drugs via the vertebral venous system, in a manner as outlined herein, may be performed. The compounds could include interleukins, cytokines, interferons, drugs, growth factors, VEGF inhibitors, monoclonal antibodies, fusion proteins, anti-angiogenic agents, chemotherapeutic agents, cytostatic agents, cancer therapeutics, viral or other vectors for delivering gene therapy or other therapeutic molecules for which delivery by perispinal administration without direct intrathecal injection would be beneficial.

One of the advantages of perispinal delivery into the interspinous space is that administration is simplified. This route is simple and safe. Hemorrhage due to the use of long or large bore needles is minimized because perispinal administration, by the subcutaneous route, requires only a short, narrow bore needle. Time-consuming and difficult epidural injection is not necessary. Local perispinal administration also has the advantage of providing a depot of therapeutic medication in the surrounding tissue, which will provide therapeutic levels of medication to the treatment site for a prolonged period of time. This decreases the necessity for another injection of medication. Additionally, administering medication locally limits the exposure of the medication to the systemic circulation, thereby decreasing renal and hepatic elimination of the medication, and decreasing exposure of the medication to systemic metabolism. All of these factors tend to increase the therapeutic half-life of the administered large molecule. Taken together, all of these forms of perispinal administration have significant clinical advantages over the various forms of systemic administration customarily used to deliver large molecules systemically. For example, intravenous administration (as conventionally performed, by infusion into the caval venous system) of infliximab is a systemic route of administration, as defined herein, and is distinguished from perispinal administration as a method to reach the brain (predominantly via the VVS) as defined herein.

For the sake of this invention, the following definitions also apply: perilesional is defined as in anatomic proximity to the site of the pathologic process being treated; and peridural is defined as in anatomic proximity to the dura of the spinal cord, but specifically excluding intrathecal injection. The "interspinous route" for the purposes of this patent, is defined as parenteral injection through the skin in or near the midline, in the interspace between two spinous processes.

This invention is distinguished from the prior art in a variety of ways, including the use and description of novel and useful new uses, methods of use, and concepts involving large molecules, including:

1. Novel uses of perispinal administration to enhance delivery of a large molecule to the brain, the eye, the retina, the auditory apparatus, the cranial nerves or the head; and
2. Novel methods of use of large molecules; and
3. Novel concepts, including:
    a. Perispinal (extrathecal) administration distinguished from systemic forms of administration and intrathecal administration;
    b. The use of the vertebral venous system to deliver large molecules to the bone brain, the eye, the retina, the auditory apparatus, the cranial nerves or the head;
    c. The use of physical maneuvers to facilitate delivery of therapeutic molecules to the brain, the eye, the retina, the auditory apparatus, the cranial nerves or the head;
    d. The use of physical positioning to influence the direction of venous flow within the vertebral venous system and thereby deliver therapeutic molecules to the brain, the eye, the retina, the auditory apparatus, the cranial nerves or the head;
    e. The use of retrograde venous perfusion to deliver therapeutic molecules to the brain, the eye, the retina, the auditory apparatus, the cranial nerves or the head;
    f The use of retrograde venous perfusion via the vertebral venous system to facilitate delivery of therapeutic molecules to the brain, the eye, the retina, the auditory apparatus, the cranial nerves or the head;
    g. The use of the vertebral venous system as a "back door" to facilitate delivery of therapeutic molecules to the brain, the eye, the retina, the auditory apparatus, the cranial nerves or the head;
    h. The use of perispinal administration to introduce a large molecule into the vertebral venous system;
    i. The use of perispinal administration to efficiently deliver large molecules to the brain, the eye, the retina, the auditory apparatus, the cranial nerves or the head.

The same methods described for the named large molecules (such as pegfilgrastim) of this invention also apply to other large molecules with a molecular weight of 2,000 daltons or greater, which may be given by perispinal administration.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

(Experimental results compiled by the inventor illustrating the efficacy of perispinal administration of a biologic are described below. More specifically, these results illustrate the ability of interspinous injection to lead to delivery of a biologic to the VVS, and thereafter to the brain, utilizing the methods of the present invention).

Experimental Results

An IRB-approved clinical trial utilizing perispinal etanercept for treatment of Alzheimer's Disease was begun by the inventor in 2004 and clinical data is available on the first 15 consecutive patients who completed more than three weeks of the clinical trial, through Nov. 7, 2005, although the clinical trial is ongoing. Data on the 6 month results is now available. A summary of the study follows:

Patients

Patients residing in the community, who had previously been diagnosed with Alzheimer's Disease by a board-certified neurologist and were clinically declining despite treatment, were recruited, without age restriction, for inclusion into a six month open-label clinical trial utilizing perispinally administered etanercept. Inclusion required that the patient meet the NINCDS-ADRDA Criteria for probable Alzheimer's disease[1]; be accompanied by a reliable caregiver; and have a previously performed MRI or CT scan consistent with a primary diagnosis of AD. All recruited patients also met the DSM-IV criteria for AD[2]. Patients were excluded if they had any of the following: active infection, multiple sclerosis (or any other demyelinating disorder), pregnancy, uncontrolled diabetes mellitus, tuberculosis, history of lymphoma, or congestive heart failure. In addition, female subjects who were premenopausal, fertile, or not on acceptable birth control; and patients with a white blood cell count<2500, hematocrit<30, or a platelet count<100,000 were excluded. Patients with vascular dementia, clinically significant neurologic disease other than Alzheimer's, or a score greater than 4 on the modified Hachinski Ischemic Rating Scale[3] were excluded. Additionally, to be eligible for study inclusion, the dosage of all CNS-active medications was required to be unchanged in the four weeks prior to study initiation and during the entire course of the clinical trial.

Study Design

Patients received etanercept (Immunex Corp.) as a solution in sterile water given by midline perispinal interspinous injection in the posterior cervical area (as previously described[4]) utilizing a thin (27 gauge) needle, followed by head down Trendelenburg positioning, once or twice per week, at a total dose ranging from 25 mg to 50 mg per week (0.5-2 cc of solution) on an open-label basis. The initial dose used was 25 mg once per week, which was modified as needed. The trial was approved by a central institutional review board. The eligible patients and their responsible caregivers provided written informed consent.

Efficacy Variables

The primary efficacy variables for cognition were three measures: the Alzheimer's Disease Assessment Scale-cognitive subscale (ADAS-Cog); the Severe Impairment Battery; the Mini-Mental State Examination (MMSE).

Patients were assessed at baseline (treatment day zero) and monthly thereafter. All patients were assessed with the MMSE. Patients with mild and moderate AD were assessed with ADAS-Cog. Patients with severe dementia were assessed with the SIB.

Measures of safety included measurement of vital signs and recording of adverse events.

Results

Study Population and Dosage

All data from all 15 patients who completed at least one follow-up evaluation time-point were analyzed. All of these patients completed the first six months of treatment. Treatment response data were unavailable for two patients, in addition to the above 15, who dropped out for non-medical reasons prior to their first monthly evaluation; these two patients were excluded from analysis. One patient whose dementia was borderline between moderate and severe was assessed with both ADAS-Cog and SIB, in addition to MMSE. The baseline characteristics of the 15 patient study population are presented in Table 1. The average dosage for the study cohort was 32±12 mg per week (n=15), and the average frequency of dosing was 1.07 times per week.

Statistical Analysis

The main efficacy analysis at 6 months is based on all 15 patients who have baseline and follow-up data.

The MMSE, ADAS-Cog, and the SIB are considered as the primary outcome measures at the end of the three month follow-up assessment. Mixed Model Linear Regression (MMLR) analyses were used to assess improvement in disease over time, as evaluated by the four outcome measures. In each analysis, time (baseline, 1, 2, 3, 4, 5 and 6 months) was entered as a fixed variable. The models were also specified with random intercepts, as the participants in this study varied across the spectrum of severity at baseline because recruitment was not limited to a range of severity. Missing data points are treated as missing and are not estimated; this was an observed data analysis.

Data were analyzed using statistical analysis software SPSS (Version 11.0.3 for Mac OS X, SPSS Inc., Chicago, Ill., USA), with $p<0.05$ indicative of statistical significance.

Efficacy

The results of treatment through six months and the statistical analysis are presented in Table 1.

TABLE 1

Summary of Mixed Model Linear Regression (MMLR) results following initiation of perispinal etanercept.

| | Measure (n) | | | | | | | |
|---|---|---|---|---|---|---|---|---|
| | Baseline Mean (SD) | Mean change at 1 month (SD) | Mean change at 2 months (SD) | Mean change at 3 months (SD) | Mean change at 4 months (SD) | Mean change at 5 months (SD) | Mean change at 6 months (SD) | Regression Analyses Results |
| MMSE (15) | 18.2 (8.8) | −.29 (1.82) | +1.07 (2.01) | +1.87 (1.99) | +2.00 (2.13) | +1.93 (2.34) | +2.13 (2.23) | $F_{(1.84)} = 39.00$, $p < .001$ |
| ADAS-cog (11) | 20.85 (10.5) | −4.28 (3.44) | −4.64 (4.36) | −4.67 (5.97) | −7.14* (4.51) | −4.52 (4.80) | −5.48 (5.08) | $F_{(1.61)} = 11.72$, $p < .002$ |
| SIB (5) | 62.5 (28.05) | +4.67 (6.35) | +8.2 (3.56) | +11.75 (6.45) | +13.6 (10.89) | +13.0 (13.69) | +16.6 (14.52) | $F_{(1.26)} = 22.60$, $p < .001$ |

Caption: Baseline raw group mean and standard deviations are presented with the mean change and SD (each participant compared to their respective baseline performance) for the 6 subsequent follow-up months.
Note:
For the ADAS-Cog, lower scores indicate clinical improvement.
*Note 2:
reduced n = 7 at this time point.
SD = Standard Deviation

TABLE 2

Patient Characteristics, at baseline, prior to perispinal etanercept treatment.

| Characteristic | Mean ± SD | Range |
|---|---|---|
| Age, in yrs. | 76.7 ± 10.9 | 52, 94 |
| Female, % (n) | 60% (9) | — |
| Duration of symptoms, in mos. | 43.1 ± 37.9 | 8, 120 |
| ADAS-Cog score (n = 11) | 20.8 ± 10.5 | 7.3, 41 |
| SIB score (n = 5) | 62.5 ± 28.05 | 28, 92 |
| MMSE score (n = 15) | 18.2 ± 8.8 | 0, 29 |
| Prior Treatments: | | |
| Memantine, % (n) | 73% (11) | — |
| Duration prior to Etanercept, in mos. | 10.6 ± 4.0 | 1.5, 15 |
| Donepezil, % (n) | 47% (7) | — |
| Duration prior to Etanercept, in mos. | 44.7 ± 47.9 | 10, 120 |
| Rivastigmine, % (n) | 27% (4) | — |
| Duration prior to Etanercept, in mos. | 5.6 ± 3.3 | 1, 8 |
| Galantamine, % (n) | 13% (2) | — |
| Duration prior to Etanercept, in mos. | 40.5 ± 6.4 | 36, 45 |
| Only 1 of the above, % (n) | 40% (6) | — |
| Memantine + a cholineserase inhibitor, % (n) | 60% (9) | — |

(End of Experimental Results).

PREFERRED EMBODIMENTS

In one preferred embodiment a patient with a clinical disorder involving the brain, the retina, the eye, the cranial nerves or hearing is treated by a perispinal injection of a large molecule, in a therapeutically effective dose, delivered by midline transcutaneous injection overlying the spine in the lower posterior neck area, with the patient sitting and head flexed forward, with immediate placement of the patient in the prone position with the plane of the examination table directed head downward about 15 degrees after the injection, and maintenance of the patient in this modified Trendelenburg prone position for several minutes after injection, in order to deliver the large molecule to the brain, the retina, the eye, the cranial nerves or the auditory apparatus via the vertebral venous system, with the dose repeated as a form of chronic therapy at intervals as often as twice per week to as little as once per three months.

In another preferred embodiment an individual with a clinical disorder involving the eye or retina, who desires to achieve improved vision or to prevent visual loss, is treated by a perispinal injection of etanercept using a 25 mg dose in solution, delivered by midline transcutaneous injection overlying the spine in the lower posterior neck area, with the patient sitting and head flexed forward, with immediate placement of the patient in the prone position with the plane of the examination table directed head downward about 15 degrees after the injection, and maintenance of the patient in this modified Trendelenburg prone position for several minutes after injection, as either a single dose, or with doses repeated as often as once per week.

In another preferred embodiment injection of a large molecule to the perispinal area is accomplished by percutaneous injection into the anatomic area between two adjacent spinous processes ("the interspinous space").

In another preferred embodiment interspinous injection is accomplished by injection through the skin.

Clinical Disorders

Patients with the following clinical disorders, or in the following clinical situations, among others, will benefit from treatment with large molecules delivered by the perispinal route without direct intrathecal injection:

Macular Degeneration. This category includes both "wet" or "dry" macular degeneration, both of which involve excess TNF and/or the participation of TNF-mediated inflammatory or degenerative pathways in their pathogenesis. Treatment of patients with these disorders with perispinal etanercept leads to visual improvement and/or slowing of disease progression. Chronic treatment regimens are necessary utilizing perispinal etanercept. Certolizumab pegol or golimumab may be used in a manner which is similar to that of etanercept, except that due to their longer half-life less frequent administration, compared to etanercept, is necessary. Etanercept, golimumab, or certolizumab pegol may be administered concurrently with memantine (delivered orally) to further reduce retinal inflammation or optic nerve damage. Also soluble TNF receptor type 1, and pegylated soluble TNF receptor type 1 may be administered by perispinal administration for treatment of this disorder. Pegapanib, ranibizumab, and bevacizumab (Avastin™, Genentech), a recombinant humanized monoclonal IgG1 antibody that binds to and inhibits the biologic activity of human vascular endothelial growth factor (VEGF), may also be administered by perispinal administration without direct intrathecal injection for both the treatment or prevention of macular degeneration and/or neovascularization and thereby produce visual improvement or prevention or delay of future visual loss. Additionally these disorders are known to involve IL-1. Therefore treatment of these disorders with an IL-1 antagonist, such as IL-1 RA (Kineret) or IL-1 Trap administered by perispinal delivery so that a therapeutically effective dose of the IL-1 antagonist reaches the vertebral venous system and thenceforth the retina, delivered utilizing a chronic treatment regimen, is an alternative treatment. Each of these molecules will need to be delivered on a chronic basis to decrease the inflammatory response which is responsible for neuronal damage in these conditions and thereby produce clinical improvement.

Diabetic Retinopathy. This condition involves excess TNF and/or the participation of TNF-mediated inflammatory or degenerative pathways in its pathogenesis. Treatment of patients with this disorder with perispinal etanercept leads to visual improvement and/or slowing of disease progression. Chronic treatment regimens are necessary utilizing perispinal etanercept. Golimumab may be used in a manner which is similar to that of etanercept, except that due to its longer half-life less frequent administration, compared to etanercept, will be necessary. Also soluble TNF receptor type 1, and pegylated soluble TNF receptor type 1 may be administered by perispinal administration for treatment of this disorder. Pegapanib, ranibizumab, and bevacizumab (Avastin™, Genentech), a recombinant humanized monoclonal IgG1 antibody that binds to and inhibits the biologic activity of human vascular endothelial growth factor (VEGF), may also be administered by perispinal administration for both the treatment or prevention of diabetic retinopathy and/or neovascularization and thereby produce visual improvement or prevention or delay of future visual loss. Additionally these disorders are known to involve IL-1. Therefore treatment of this disorder with an IL-1 antagonist, such as IL-1 RA (Kineret) or IL-1 Trap administered by perispinal delivery so that a therapeutically effective dose of the IL-1 antagonist reaches the vertebral venous system and thenceforth the retina, delivered utilizing a chronic treatment regimen, is an alternative treatment. Each of these molecules will need to be delivered on a chronic basis to decrease the inflammatory response which is responsible for neuronal damage in these conditions and thereby produce clinical improvement.

Glaucoma. This condition involves excess TNF and/or the participation of TNF-mediated inflammatory or degenerative pathways in its pathogenesis. Treatment of patients with this disorder with perispinal etanercept leads to visual improvement and/or slowing of disease progression. Chronic treatment regimens are necessary utilizing perispinal etanercept. Golimumab may be used in a manner which is similar to that of etanercept, except that due to its longer half-life less frequent administration, compared to etanercept, will be necessary. Also soluble TNF receptor type 1, and pegylated soluble TNF receptor type 1 may be administered by perispinal administration for treatment of this disorder. Etanercept or golimumab may be administered concurrently with memantine (delivered orally) to further reduce retinal inflammation or optic nerve damage. Additionally these disorders are known to involve IL-1. Therefore treatment of this disorder with an IL-1 antagonist, such as IL-1 RA (Kineret) or IL-1 Trap administered by perispinal delivery so that a therapeutically effective dose of the IL-1 antagonist reaches the vertebral venous system and thenceforth the retina, delivered utilizing a chronic treatment regimen, is an alternative treatment. Each of these molecules will need to be delivered on a chronic basis to decrease the inflammatory response which is responsible for neuronal damage in these conditions and thereby produce clinical improvement.

Retinitis Pigmentosa. This condition involves excess TNF and/or the participation of TNF-mediated inflammatory or degenerative pathways in its pathogenesis. Treatment of patients with this disorder with perispinal etanercept leads to visual improvement and/or slowing of disease progression. Chronic treatment regimens are necessary utilizing perispinal etanercept. Golimumab may be used in a manner which is similar to that of etanercept, except that due to its longer half-life less frequent administration, compared to etanercept, will be necessary. Also soluble TNF receptor type 1, and pegylated soluble TNF receptor type 1, or Certolizumab pegol may be administered by perispinal administration for treatment of this disorder. Etanercept or golimumab may be administered concurrently with memantine (delivered orally) to further reduce retinal inflammation or optic nerve damage. Additionally these disorders are known to involve IL-1. Therefore treatment of this disorder with an IL-1 antagonist, such as IL-1 RA (Kineret) or IL-1 Trap administered by perispinal delivery so that a therapeutically effective dose of the IL-1 antagonist reaches the vertebral venous system and thenceforth the retina, delivered utilizing a chronic treatment regimen, is an alternative treatment. Each of these molecules will need to be delivered on a chronic basis to decrease the inflammatory response which is responsible for neuronal damage in these conditions and thereby produce clinical improvement.

Dementia. This category includes, but is not limited to Alzheimer's Disease, amnestic mild cognitive impairment, vascular dementia, and mixed dementia. The inventor has clinical experience utilizing etanercept delivered by perispinal extrathecal administration demonstrating clinical benefit for each of these conditions. Humans with these disorders are amenable to treatment utilizing perispinal administration without direct intrathecal injection of large molecules, including but not limited to etanercept, golimumab, certolizumab pegol and other anti-TNF molecules (as illustrated by the experimental results included herein), MRA(Roche, Chugai), a humanized anti-IL-6 receptor monoclonal antibody; anti-IL-1 molecules; immune globulin (such as IVIG, Baxter, being a mixture of immune globulins, including anti-amyloid antibodies) and other large molecules with immune activity. Golimumab is used by perispinal administration at a dose ranging from 5 mg to 100 mg, with a dosing interval from weekly to once per three months. The usual starting dose of golimumab for a human with dementia such as Alzheimer's Disease is 10 mg to 25 mg once per two weeks, with dosage titrated as needed within the above dosing guidelines.

Malignant Tumors metastatic to the spine: Malignant tumors metastatic to the spine may be treated by the use of biologics delivered via the VVS. Access to the VVS may be accomplished by perispinal administration, in the general manner as described herein for etanercept. There is also experimental evidence that both pro-inflammatory cytokines and their antagonists can be effective in the treatment of malignancies. This has been demonstrated most clearly with TNF, where high doses have been found to lead to tumor death; and, also with TNF blockers that demonstrate a therapeutic benefit in treating certain malignancies. This apparent paradox is explained by dose effects wherein a high dosage of TNF may lead to tumor death, whereas a low dosage may be tumor promoting. Therefore this invention includes any of the following molecules used individually: etanercept, golimumab, certolizumab pegol or pegsunercept; and, additionally, includes other biologic TNF antagonists, including infliximab, when delivered by perispinal extrathecal administration. The dosage of etanercept for this application ranges from 25 mg to 100 mg; the dosage of golimumab for this application ranges from 10 mg to 200 mg, and will most often range between 25 mg and 100 mg.

Malignant-intracranial tumors. This category includes both primary brain tumors, such as glioblastoma multiforme and tumors metastatic to the brain, all of which involve excess VEGF and/or the participation of VEGF-mediated angiogenesis, or immune mechanisms in their pathogenesis. Treatment of patients with these disorders with perispinal administration without direct intrathecal injection of a large molecule which inhibits VEGF; or which is directly toxic to a tumor, including, but not limited to monoclonal antibodies, or monclonal antibody-antitumor conjugates; or which otherwise positively affects immune mechanisms; including, but not limited to such large molecules as etanercept, certolizumab pegol, IL-1 Trap, Kineret®, bevacizumab, pegaptanib, ranibizumab, Zevalin®, Mylotarg®, Campath®, HumaSpect®, panitumumab, trastuzumab, Ontak®, Simulect®, Zenapax®, leads to reduced tumor growth, tumor death, and/or slowing of disease progression. CNS lymphomas and other CNS malignancies may be treated by perispinal administration without direct intrathecal injection of rituximab, temozolomide, yttrium-90 ibritummomab tiuxetan, iodine-131 tositumomab, epratuzumab, alemtuzumab, or natalizumab. Chronic or recurrent treatment regimens may be necessary to deliver these large molecules to the intracranial tumor via perispinal administration without direct intrathecal administration. Avoidance of intrathecal use is safer, has fewer side effects, avoids CSF leak from a dural tear, and eliminates the need for chronic intrathecal delivery systems, such as pumps. Small molecules may also be administered by perispinal delivery without direct intrathecal injection as discussed in a preceding section. Perispinal delivery of small molecules allows the achievement of a higher concentration of the small molecule in the brain and therefore in an intracranial malignant tumor. This is particularly advantageous for small molecules which have therapeutic activity for the treatment of cancer, such as a receptor tyrosine kinase inhibitor. Erlotinib is a small molecule epidermal growth factor receptor (EGFR) inhibitor which is conventionally used for treatment of non-small cell lung cancer (NSCLC). Gefitinib is another tyrosine kinase inhibitor which may be formulated in solution and therefore delivered by perispinal administration. This invention includes the use of erlotinib in solution, gefitinib in solution, or an erlotinib or gefitinib derivative or other receptor tyrosine kinase inhibitors, given by perispinal administration for treatment of intracranial malignant tumors, including lung cancer metastatic to the brain, or metastases to the brain of other malignant tumors which overexpress EGFR, or for treatment of primary brain tumors, including glioblastoma multiforme. Receptor tyrosine kinase is a protein product of the EGFR gene. Inhibition of EGFR-associated tyrosine kinase is a method of treating solid tumors, including NSCLC, and perispinal administration of these agents is a method of the present invention to increase delivery of these agents to intracranial tumors. Erlotinib has a MW of 429. Perispinal administration of the molecules of the present invention leading to delivery of a therapeutically effective amount of said molecule to the brain, the eye, or an intracranial tumor is distinguished from the systemic administration of said molecules.

Multiple Sclerosis. This immune-mediated disease of the brain is conventionally treated by systemic administration of Copaxone® (glatiramer acetate), or interferons, including Avonex®, Rebif®, and Betaseron®. Perispinal administration of these molecules, and other large molecules, including, but not limited to, rituximab, MRA, Intron A®, PEG-Intron®, Infergen®, and Actimmune® will allow therapeutically effective amounts of these large molecules to reach to brain of a human with this disorder, thereby leading to clinical improvement or a decrease in the rate of disease progression.

Hearing Loss. Hearing loss occurs in humans in many forms. Hearing is essential to the normal conduct of one's daily activities and people with impaired hearing have many difficulties. Hearing loss can date from birth; it can be acquired later in life; or it can be the result of trauma, accident, disease, or a toxic effect of a medication. It can be genetic, either as a solitary disorder or as part of a complex syndrome. Hearing loss is one of the most common chronic neurological impairments, estimated to affect about 4 percent of those under 45 in the United States, and about 29 percent of those 65 years or older.

As defined herein, the neuronal auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids.

The pathogenetic mechanism of most forms of hearing loss has yet to be fully defined. The subjects of this patent include central hearing loss due to lesions of the central auditory pathway; sensorineural hearing loss; sudden hearing loss; autoimmune hearing loss; presbycusis; idiopathic hearing loss; and other forms of hearing loss which are not thought to be primarily due to disorders of conduction (such as a ruptured tympanic membrane).

Humans react to sounds that are transduced into neurally conducted impulses through the action of neuroepithelial cells (hair cells) and spiral ganglion cells (neurons) in the inner ear. These impulses are transmitted along the cochlear division of the eighth cranial nerve into the brainstem and the central auditory pathways.

Presbycusis, or age-related hearing loss, is a type of deafness which affects one-third of the population over the age of 75. Presbycusis is known to be associated with neuronal damage, including loss of neuroepithelial (hair) cells and associated neurons (see Schuknecht reference). The exact mechanism of presbycusis is unknown, and has long been thought to be multifactorial. Inflammation is not widely recognized as a significant factor in the pathogenesis of presbycusis. Yet a previous study did suggest that genes encoded by the major histocompatibility complex (MHC) had a role in certain hearing disorders. (Bernstein, Acta Otolaryngol 1996 September; 116(5):666-71). The MHC is known to be central to the immune response and inflammation. Normal hearing is dependant upon proper neuronal function, and may be altered by autoimmune disorders or other types of inflammation. The neuronal auditory apparatus is protected by the blood-brain barrier. Therefore delivery of large molecules for therapeutic purposes by the systemic route is inhibited by the BBB. Delivery of large molecules, in particular anti-TNF biologics, including golimumab and others, or other biologics which reduce inflammation, by perispinal administration, as illustrated herein, is an effective way to treat various types of hearing loss, including sensorineural hearing loss and presbycusis.

Neuropsychiatric Disorders. Psychiatric disorders which have a biological basis, such as depression and schizophrenia, can be treated by the methods of the present invention. In particular, humans with these disorders are amenable to treatment utilizing perispinal administration without direct intrathecal injection of large molecules, including but not limited to anti-TNF molecules, including golimumab and others (as illustrated by the experimental results included herein), MRA(Roche, Chugai), a humanized anti-IL-6 receptor monoclonal antibody; anti-IL-1 molecules; and other large molecules with immune activity.

Brain Disorders. Brain disorders which have a biological basis, such as seizure disorders, Huntington's Chorea, Parkinson's Disease, and other brain disorders, can be treated by the methods of the present invention. In particular, humans with these disorders are amenable to treatment utilizing perispinal administration without direct intrathecal injection of large molecules, including but not limited to anti-TNF molecules, including golimumab and others (as illustrated by the experimental results included herein), MRA(Roche, Chugai), a humanized anti-IL-6 receptor monoclonal antibody; anti-IL-1 molecules; and other large molecules with immune activity.

Disc-related Pain, including low back pain, cervical radiculopathy, discogenic pain, sciatica, and pain associated with degenerative disc disease. The author has considerable experience utilizing perispinal etanercept for the treatment of low back pain, discogenic pain, cervical radiculopathy, sciatica and related disorders which has established the efficacy of this novel method of treatment. Certolizumab pegol and golimumab given to a human or other mammal by perispinal administration is also effective for treating these disorders.

Dosages and Routes of Administration

The therapeutically effective dosage of a large molecule used for perispinal administration will in general be 10% to 100% of the dosage used as a single dose for systemic administration. This dosage used for systemic administration is well known by those skilled in the art as it is specified in the FDA approved literature which accompanies each of these biologics, since each is FDA approved for other clinical uses. For example, if the usual dose when administered systemically is 50 mg, then the dose used for perispinal administration will usually be between 5 mg and 50 mg.

Golimumab may be administered to the perispinal area by interspinous injection at a dose of 5 mg to 100 mg given from once per week to once per 3 months. Starting doses of 10 mg-25 mg every other week are given for treatment of dementia.

Etanercept may be administered in the perispinal area subcutaneously in the human and the dosage level is in the range of 10 mg to 100 mg per dose, with dosage intervals as short as one day.

Pegaptanib may be administered perispinally in a therapeutically effective dose. The dosage of pegaptanib may vary from 0.2 mg to 10 mg per dose.

Ranibizumab may be administered in a therapeutically effective dose in the same ways as detailed for etanercept. The dosage of ranibizumb may vary from 100 micrograms to 3000 micrograms. For treating ocular neovascularization the most common dosage regimen is 800 micrograms of ranibizumab administered by perispinal injection every 28 days for four doses. It will be appreciated by one of skill in the art that appropriate dosages of the compounds, and compositions comprising the compounds, can vary from patient to patient. The determination of the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

6. ADVANTAGES OF THE PRESENT INVENTION

Accordingly, an advantage of the present invention is that it provides for the delivery of a large molecule to the vertebral venous system and thenceforth to the brain, the retina, the eye, the cranial nerves and the auditory apparatus as a new biologic treatment of humans with a clinical disorder of the brain, the retina, the eye, the cranial nerves, or hearing; such that the use of the biologic will result in clinical improvement, or will slow progression of the underlying pathologic process.

Accordingly, an advantage of the present invention is that it provides for the delivery of golimumab to the vertebral venous system and thenceforth to the brain, the retina, the eye, the cranial nerves and the auditory apparatus as a new biologic treatment of humans with a clinical disorder of the brain, the retina, the eye, the cranial nerves, or hearing; such that the use of golimumab will result in clinical improvement, or will slow progression of the underlying pathologic process.

Another advantage of the present invention is that it provides for a biologic delivered by perispinal administration, thereby delivering the biologic into the vertebral venous system and thenceforth the brain, the retina, the eye, the auditory apparatus or the cranial nerves, which, when compared to systemic administration, produces one or more of the following: greater efficacy; more rapid onset; longer duration of action; improved delivery to the CNS; or fewer side effects.

Another advantage of the present invention is that it provides for one of a group of biologics, as specified herein, which affect neuronal or immune function, delivered by retrograde venous flow through the vertebral venous system into the cranial venous system, thereby facilitating delivery of the biologic to the brain, the retina, the eye, the cranial nerves and the auditory apparatus for therapeutic purposes.

Accordingly, an advantage of the present invention is that it provides for the delivery of erlotinib to the vertebral venous system and thenceforth to a malignant intracranial tumor as a new biologic treatment of humans; such that the use of erlotinib will result in clinical improvement, or will slow progression of the cancer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

REFERENCES

Patents:
U.S. Pat. No. 6,015,557 Tumor necrosis factor antagonists for the treatment of neurological disorders, filed Mar. 23, 1999, issued Jan. 18, 2000. Additional U.S. Pat. Nos.: 6,177,077; 6,379,666; 6,419,934; 6,419,944; 6,423,321; 6,428,787; 6,471,961; 6,537,549; 6,623,736.

Additional References:
42. Ye J, Yang L, Del Bigio, et. al. Retrograde cerebral perfusion provides limited distribution of blood flow to the bone marrow: a study in pigs. J Thorac Cardiovasc Surg. 1997 October; 114 (4):660-5.
43. Edsbagge M, Tisell M, Jacobsson L, Wikkelso C. Spinal CSF absorption in healthy individuals. Am J Physiol Regul Integr Comp Physiol 287:R1450-1455, 2004.
44. Gisolf J, van Lieshout J, van Heusden K, et. al. Human cerebral venous outflow pathway depends on posture and central venous pressure. J Physiol 560.1:317-327(2004).
45. Ruiz D, Gailloud P, Rufenacht D, et. al. The craniocervical venous system in relation to cerebral venous drainage. Am J Neuroradiol 23:1500-1508, October 2002.
46. Ibukuro K, Fukuda H, Mori K, Inoue Y. Topographic anatomy of the vertebral venous system in the thoracic inlet. Am J Radiology 176:1059-1065, April 2001.
47. Batson O V. The function of the vertebral veins and their role in the spread of metastases. Ann Surg 1940: 112:138-149.
48. Batson O V. The vertebral vein system. AJ Radiology 1957 78:195-212.
49. Anderson R. Diodrast studies of the vertebral and cranial venous systems. J Neurosurg 1951:8:411-422.
50. Groen R, du Toit D, Phillips F, et. al. Anatomical and Pathological Considerations in Percutaneous Vertebroplasty and Kyphoplasty: A reappraisal of the vertebral venous system. Spine 29(13): 1465-1471 (2004).
51. Byrod G, Rydevik B, Johansson B R, Olmarker K. Transport of epidurally applied horseradish peroxidase to the endoneurial space of dorsal root ganglia: a light and electron microscopic study. J Peripher Nerv Syst. 2000 December;5(4):218-26.
52. Byrod G, Olmarker K, Konno S, Larsson K, Takahashi K, Rydevik B. A rapid transport route between the epidural space and the intraneural capillaries of the nerve roots. Spine. 1995 January 15; 20(2):138-43.
53. Olmarker K, Larsson K. Tumor necrosis factor alpha and nucleus-pulposus-induced nerve root injury. Spine. 1998 December 1; 23(23):2538-44.
54. Lirk P, Moriggl B, Colvin J, Keller C, Kirchmair L, Rieder J, Kolbitsch C. The incidence of lumbar ligamentum flavum midline gaps. Anesth Analg. 2004 April; 98(4):1178-80.
55. Lirk P, Kolbitsch C, Putz G, Colvin J, Colvin H P, Lorenz I, Keller C, Kirchmair L, Rieder J, Moriggl B. Cervical and high thoracic ligamentum flavum frequently fails to fuse in the midline. Anesthesiology. 2003 December; 99(6):1387-90.
56. Breschet, G. Recherches anatomiques, physiologiques et pathologiques sur le systeme veineux et specialement sur les cavaux veineux des os. Villaret et Cie, Paris, 1828-1832.
57. Clemens, H. J., *Die Venensysteme der menschlichen Wirbsèaule; Morphologie und funktionelle Bedeutung.* 1961, Berlin: De Gruyter. 61 p.
58. Vogelsang, H., Intraosseous spinal venography. 1970, Amsterdam: Excerpta Medica. 117 p. 59. Herlihy, W. F., *Revision of the venous system: the role of the vertebral veins.* Med J Austr, 1947. 1(22): p. 661-72.
60. Robinson, W. H., M. C. Genovese, and L. W. Moreland, *Demyelinating and neurologic events reported in association with tumor necrosis factor alpha antagonism: by what mechanisms could tumor necrosis factor alpha antagonists improve rheumatoid arthritis but exacerbate multiple sclerosis?* Arthritis Rheum, 2001. 44(9): p. 1977-83.
61. Bohac D, Burke W, Cotter R, Jilian Z, Potter J, Gendelman H. A 24-week randomized, double-blind, placebo-controlled study of the efficacy and tolerability of TNFR: FC (etanercept) in the treatment of dementia of the Alzheimer type. Proceedings of the 8th International Conference on Alzheimer's Disease and Related Disorders; 2002, Jul. 20-25, Stockholm, Sweden 2002:Abstract No 315.
62. Markomichelakis, N. N., P. G Theodossiadis, and P. P. Sfikakis, *Regression of neovascular age-related macular degeneration following infliximab therapy.* Am J Ophthalmol, 2005. 139(3): p. 537-40.
63. Tobinick, E. and S. Davoodifar, *Efficacy of etanercept delivered by perispinal administration for chronic back and/or neck disc-related pain: a study of clinical observations in* 143 *patients.* Curr Med Res Opin, 2004. 20(7): p. 1075-85.
64. Tobinick, E. L. and S. Britschgi-Davoodifar, *Perispinal TNF-alpha inhibition for discogenic pain.* Swiss Med Wkly, 2003. 133(11-12): p. 170-7.

What is claimed is:
1. A method for delivering a biologic to a human with Alzheimer's-related dementia, comprising the steps of administering said biologic parenterally into the perispinal space of said human without direct intrathecal injection, and positioning said human in a Trendelenburg position.
2. The method of claim 1, wherein said biologic is etanercept.
3. The method of claim 1, wherein said biologic is golimumab.
4. The method of claim 1, wherein said biologic is immune globulin.

5. The method of claim 1, wherein said biologic is bapineuzumab.

6. The method of claim 1, wherein said administered biologic reaches the brain by retrograde blood flow, and thereby bypasses the blood-brain barrier to reach the brain.

7. The method of claim 1, wherein the biologic is certolizumab pegol.

* * * * *